(12) United States Patent
Kim

(10) Patent No.: US 10,072,286 B2
(45) Date of Patent: Sep. 11, 2018

(54) MARKER FOR GENERATING BINDING INFORMATION ON BIOMOLECULES AND NUCLEIC ACIDS, PREPARATION METHOD THEREFOR, AND METHOD AND APPARATUS FOR ANALYZING BIOMOLECULE BY USING SAME

(71) Applicant: BIOIS CORP., Seoul (KR)

(72) Inventor: Sung-Chun Kim, Seoul (KR)

( * ) Notice: Subject to any disclaimer, the term of this patent is extended or adjusted under 35 U.S.C. 154(b) by 183 days.

(21) Appl. No.: 15/031,009

(22) PCT Filed: May 8, 2014

(86) PCT No.: PCT/KR2014/004107
§ 371 (c)(1),
(2) Date: Jul. 19, 2016

(87) PCT Pub. No.: WO2015/060511
PCT Pub. Date: Apr. 30, 2015

(65) Prior Publication Data
US 2016/0362720 A1 Dec. 15, 2016

(30) Foreign Application Priority Data

Oct. 22, 2013 (KR) .......................... 10-2013-0125675

(51) Int. Cl.
*C12Q 1/6811* (2018.01)
(52) U.S. Cl.
CPC ........ *C12Q 1/6811* (2013.01); *G01N 2496/80* (2013.01); *G01N 2570/00* (2013.01)
(58) Field of Classification Search
CPC ...... C12Q 1/6811; C12N 15/115; C40B 40/00
See application file for complete search history.

(56) References Cited

U.S. PATENT DOCUMENTS

| 8,597,884 | B2 * | 12/2013 | Dore | ........................ | C12N 1/06 435/18 |
| 2002/0177218 | A1 * | 11/2002 | Fang | .................. | G01N 33/6872 435/252.3 |
| 2009/0075828 | A1 | 3/2009 | Fisher et al. | ....................... | 506/7 |
| 2009/0082217 | A1 * | 3/2009 | Smolke | .............. | C12N 15/1048 506/9 |
| 2010/0029492 | A1 * | 2/2010 | Kim | ...................... | C12Q 1/6834 506/7 |
| 2011/0262922 | A1 * | 10/2011 | Chae | .................. | G01N 33/5308 435/6.12 |
| 2013/0059292 | A1 * | 3/2013 | Kim | ................. | G01N 33/54306 435/5 |

FOREIGN PATENT DOCUMENTS

| JP | 2012-125200 | 7/2012 | ............... C12Q 1/68 |
| KR | 10-2006-0029771 | 4/2006 | ............... C12Q 1/68 |
| KR | 10-2008-0108652 | 12/2008 | ............... C12Q 1/68 |
| WO | WO 2005/090546 | 9/2005 | ............... C12M 1/34 |
| WO | WO 2005/108609 | 11/2005 | ............... C12Q 1/68 |
| WO | WO 2013/116527 | * 8/2013 | |

OTHER PUBLICATIONS

Stewart et al, Identifying Protein Variants with Cross-Reactive Aptamer Arrays, 2011, ChemBioChem, 12, 2021-2024. (Year: 2011).*
Lau et al, Quality Control Certification of RNA Aptamer-Based Detection, 2013, ChemBioChem, 14, 987-992. (Year: 2013).*
Blind et al, Aptamer Selection Technology and Recent Advances, 2015. Molecular Therapy—Nucleic Acids, 4, e223, pp. 1-7. (Year: 2015).*
International Search Report (ISR) dated Oct. 23, 2014 in PCT/KR2014/004107 published as WO 2015/060511 with English Translation.
Wilson, et al. (2005) "Simpleaffy: a BioConductor package for Affymetrix Quality Control and data analysis.", *Bioinformatics Applications Note*, vol. 21(18):3683-3685.
McCauley, T. G., et al. "Aptamer-based biosensor arrays for detection and quantification of biological macromolecules", Analytical Biochemistry, 319, 2003, pp. 244-250.
You, Q., et al. "Proteomic analysis of plasma from Holstein cows testing positive for *Mycobacterium avium* subsp. *Paratuberculosis* (MAP)", Veterinary Immunology and Immunopathology, 148, 2012, pp. 243-251.
Extended European Search Report from corresponding European Patent Application No. EP 14855454, dated Apr. 28, 2017.

* cited by examiner

*Primary Examiner* — Narayan K Bhat
(74) *Attorney, Agent, or Firm* — Harness, Dickey & Pierce, P.L.C.

(57) ABSTRACT

The present invention relates to a reference substance and a nucleic acid chip for generating binding information on biomolecules and analysis single-stranded nucleic acids in a biosample composed of biomolecules; a method for preparing the same; and a method for analyzing biomolecules using the same, and the reference substance and the nucleic acid chip can be used for analyzing the biological significance of the biomolecules. In addition, the present invention relates to a method for preparing an external reference substance and a biochip for generating the binding information on biomolecules and ligands; and a method for analyzing biomolecules using the same. The external reference substance and the biochip of the present invention can be used in the field of analyzing the biological significance of the biomolecules.

6 Claims, 16 Drawing Sheets
Specification includes a Sequence Listing.

MARKER FOR GENERATING BINDING INFORMATION ON BIOMOLECULES AND NUCLEIC ACIDS, PREPARATION METHOD THEREFOR, AND METHOD AND APPARATUS FOR ANALYZING BIOMOLECULE BY USING SAME

CROSS-REFERENCE TO RELATED APPLICATIONS

This application is a national phase application of PCT Application No. PCT/KR2014/004107, filed on May 8, 2014, which claims the benefit and priority of Korean Patent Application No. 10-2013-0125675, filed Oct. 22, 2013. The entire disclosures of the applications identified in this paragraph are incorporated herein by reference.

FIELD

The present invention relates, in general, to a reference substance and a nucleic acid chip for predicting biological significance of biomolecules in a biosample composed of biomolecules, a method for preparing the same, and a method and an apparatus for analyzing biomolecules using the same. In addition, the present invention relates, in general, to a method for preparing an external marker (that is, external reference substance) and a biochip for generating binding information on biomolecules and ligands, and a method for analyzing biomolecules using the same.

BACKGROUND

In accordance with advances in physics, biochemistry, and bioinformatics, many technologies for obtaining profiles of a large number of biomolecules (proteins and carbohydrates) constituting a biosample have been developed. However, in spite of such technologies, there is a considerable need for novel and efficient methods and apparatuses due to problems regarding the use, maintenance cost, feasibility, accuracy, sensitivity, required testing times, and process automation ability of the existing methods or devices.

A method for generating comprehensive information on quantitative states of these biomolecules, that is, a profile of the biomolecules in the biosample containing the biomolecules, which is not an ultimate object but is a means for achieving the object, may be usefully used to identify microorganisms, cells, tissues, and the like, such that the method for generating a profile has been widely applied to medicine, veterinary medicine, environmental engineering, food engineering, agriculture, and the like.

A clinical decision support system (CDSS) for analyzing biological significance using the profile of the biomolecules in a biosample is a system for supporting a decision making process by a doctor, associated with diagnosis and treatment of a patient. The clinical decision support system is largely divided into a case-based machine learning inference system and an expert system. The case-based machine learning inference system is a system of collecting clinical information of patients with diagnosed diseases and biological information, that is, profile data on the biomolecules, and then inferring or determining a disease on the basis of given clinical information, biological information, and the like, using machine learning. The expert system is a system of diagnosing a disease using a rule predetermined by a medical expert.

A nucleic acid is a linear multimer in which nucleotides are linked by covalent bonds, wherein the nucleotide is a small organic compound composed of a phosphoric acid, a sugar, and a purine (adenine or guanine) or a pyrimidine (cytosine, thymine, or uracil). The nucleic acid exists in single-stranded form or double-stranded form, and a single-stranded nucleic acid forms a unique stereoscopic structure by hydrogen bonds and interactions between the nucleotides under specific physical conditions, and this stereoscopic structure is determined by a base sequence of the single strand.

In general, nucleic acids such as deoxyribonucleic acids (DNAs) and ribonucleic acids (RNAs) are information storage molecules for expression of proteins serving as components of cell structures or having activities such as enzymes, and the like. Since it was reported in 1982 that RNA can also have an enzyme activity by formation of a specific structure, many reports on structural characteristics of the nucleic acids and specific functions depending on the structural characteristics have been reported.

Nucleic acid consists of repeating units of four bases to form various stereoscopic structures with high diversity, and the nucleic acids form complexes through interaction with specific substances, such that this stereoscopic structure is stabilized.

Since nucleic acid may serve as a single-stranded nucleic acid (ligand) for molecules including proteins, nucleic acids binding to specific substances with high binding affinity and specificity are selected from a combinatorial library of single-stranded nucleic acids arranged in various base sequences through a predetermined selection process and through a base sequencing process.

A method for selecting a nucleic acid binding to a specific substance is referred to as systematic evolution of ligand by exponential enrichment (SELEX), and the selected nucleic acid is referred to as an aptamer (Tuerk C. and Gold L.; Science, 249, pp 505-510, 1990).

Nucleic acids (aptamers) capable of binding to various biomolecules, such as proteins capable of binding to nucleic acids in a natural state, or proteins that do not bind to the nucleic acids, have been selected through the SELEX as described above.

However, a method for selecting a nucleic acid through the existing SELEX is a method for selecting a nucleic acid (aptamer) having high binding affinity by preferentially mass-producing and purifying a corresponding protein (specific substance) prior to selection of a nucleic acid specifically binding to the specific substance (for example, the protein), reacting a library of single-stranded nucleic acids with the produced protein, and repeating selection and amplification. In this method, first, it was essential to secure the specific substance for selecting the nucleic acid. Therefore, in the method for selecting a nucleic acid through the SELEX according to the related art, a technical idea of selecting and using nucleic acids as a group having significance in a group of numerous unknown biomolecules contained in the biosample was not recognized. Biomolecule-single-stranded nucleic acid complexes may be selected by various methods. For example, a method for fixing the biomolecule to harvest a complex, and washing the complex, a capillary electrophoresis method, and the like, may be used.

Profiles of biomolecules including unknown molecules constituting tissues, cell mass, cells, microorganisms, and the like, which are biosamples, have been made by various methods using physical and chemical properties thereof. In general, a profile of biomolecules, which is a quantitative state of the biomolecules, in the biosample has been confirmed by performing electrophoresis on the biomolecules using molecular weights or pI values thereof.

In addition, a method for analyzing a profile to determine useful biomolecules, separating the useful biomolecules, and confirming constituent ingredients of the separated biomolecules using matrix assisted laser desorption/ionization-time spectroscopy of flight (MALDI-TOF), or the like, has been performed. Recently, various research into protein profiles has been conducted by surface-enhanced laser desorption/ionization time of flight mass spectrometry (SELDI-TOFMS) (Adam et al., Cancer Research, 62, 3609-3614. 2002; Li et al., Clinical Chemistry, 48, 1296-1304. 2002; and Petricoin et al., The Lancet, 359, 572-577. 2002).

Also recently, protein chips or aptamer chips have been developed and used by a high throughput screening method for proteomes (Smith et al., Mol. Cell Protomics, 11-18. 2003; and McCauley et al., Anal. Biochem., 319(2), 244-250. 2003). As a supporter used in the high throughput screening method as described above, there are a glass slide, a sensing surface of a biosensor, beads, nanoparticles, and the like.

Since arrangement of an antibody on a protein chip is known, the protein chip may be used to identify and quantify a specific substance. As a method for preparing a protein chip, there is a method of spotting an antibody to fix the antibody using a microarrayer. A protein chip sensing technology should be able to sense signals generated at very weak intensities in a state the protein chip is designed to integrate various antibodies at a high density on a small area in order to provide as much information as possible with one chip. Further, as bio-information of proteins is expanding, a degree of integration of the protein chip is also increasing, such that a novel method capable of rapidly and accurately quantitatively detecting a protein is required.

As a detection method, laser induced fluorescence spectroscopy has been mainly used up to now, and an electrochemical detection method, or the like, has been developed. A method for generating and analyzing a profile of specific proteins in a biosample using a protein chip has been developed through various processes as described above, but there are problems in that expensive apparatuses and reagents are used, and complicated procedures should be performed, etc., and there is a limitation in that the protein chip is applicable only to antigenic molecules.

An aptamer chip is different from the protein chip in that an aptamer (nucleic acid) is used instead of the antibody in the protein chip, and other factors of the aptamer chip are significantly similar to those of the protein chip.

As described above, methods for generating a quantitative state, that is, a profile, of biomolecules in a biosample using the protein chip and the aptamer chip have been developed, but there are problems in that expensive apparatuses and reagents are used, and complicated procedures should be performed, and the like. Particularly, there is a limitation in that protein chips or aptamer chips may be restrictively prepared only with respect to already known proteins from which antibodies or aptamers may be prepared.

Although a biosample is known to be composed of millions of proteins, only tens of thousands of proteins are identified. Therefore, there is a considerable need for a technology of generating a quantitative state, that is, a profile of unknown biomolecules such as unknown proteins in a biosample.

The present inventor suggested reverse-SELEX for generating a profile for proteome (see Korean Patent No. 10-0670799), an aptamer-based nucleic acid chip (see Korean Patent No. 10-0464225), a method for analyzing biological significance using an aptamer-based nucleic acid chip (see Korean Patent No. 10-0923048), and the like, but there were problems in that a suitable reference substance and a quality control method at the time of high throughput screening in order to generate proteome profiles were not suggested, and thus, it is impossible to perform suitable quality control upon generating and analyzing the profile. Therefore, the present invention was suggested in order to solve the problems as described above.

In research into a technology capable of entirely analyzing biomolecules in a biosample, analysis of profiles of biomolecules medically associated with diseases may be used to identify biomolecules that can serve as diagnostic markers, can be used to monitor therapeutic results, can play important roles in the outbreak or the progressions of diseases, are related to disease sensitivity, and can become target molecules for novel drug development.

DISCLOSURE

Technical Problem

Accordingly, the present invention has been made keeping in mind the above problems occurring in the related art, and the present invention is intended to propose a reference substance and a nucleic acid chip for generating binding information on biomolecules and analysis single-stranded nucleic acids in a biosample composed of two or more biomolecules while performing internal quality control, a method for preparing the same, and a method and an apparatus for analyzing biomolecules using the same, such that various biological significance including disease information associated with the biomolecules may be analyzed from the binding information efficiently formed using the same.

In addition, the present invention is intended to propose an external reference substance and a biochip capable of generating binding information on biomolecules contained in a biosample and ligands, such that biological significance including disease information associated with the biomolecules may be analyzed from the binding information efficiently formed using the same.

Technical Solution

In order to achieve the above object, according to one aspect of the present invention, there is provided a method for analyzing a biomolecule by an analysis single-stranded nucleic acid, wherein a quality control reference substance for analyzing an analysis single-stranded nucleic acid binding to biomolecules in a biosample composed of two or more biomolecules is used, and the binding single-stranded nucleic acid is selected from a nucleic acid library composed of random single-stranded nucleic acids having random base sequences, whereby internal quality control is performed by analyzing a quality control single-stranded nucleic acid using a nucleic acid analysis method.

According to another aspect of the present invention, there is provided a nucleic acid chip, wherein capture probes synthesized using base sequences of a binding single-stranded nucleic acid and a quality control single-stranded nucleic acid are affixed onto a supporter, and binding information on the binding single-stranded nucleic acid and the quality control single-stranded nucleic acid for selecting an analysis single-stranded nucleic acid is formed.

According to another aspect of the present invention, there is provided a method for analyzing biomolecules, wherein a quality control reference substance for analyzing biomolecules in a biosample using an analysis single-stranded nucleic acid is used, and internal quality control is performed by analyzing a quality control single-stranded nucleic acid using a nucleic acid analysis method.

According to another aspect of the present invention, there is provided a method for analyzing biomolecules, wherein a protein chip is analyzed using a target probe prepared by mixing an analysis target probe and a comparison target probe with each other, the analysis target probe being prepared by reacting an analysis single-stranded nucleic acid with biomolecules in a biosample and a comparison target probe being prepared by reacting the analysis single-stranded nucleic acid with biomolecules in a control biosample.

According to another aspect of the present invention, there is provided a nucleic acid chip, wherein capture probes prepared using base sequences of analysis single-stranded nucleic acids and quality control single-stranded nucleic acids are affixed onto a support, and the nucleic acid chip is used to generate binding information on biomolecules and the analysis single-stranded nucleic acids for analyzing biological significance of the biomolecules in the biosample.

According to another aspect of the present invention, there is provided a reference substance, wherein the reference substance is composed of external molecules that are not contained in a biosample, and used for quality control of an analysis process for analyzing biological significance of biomolecules in the biosample as an analysis single-stranded nucleic acid, and for quantitative analysis of the biomolecules contained in the biosample.

According to another aspect of the present invention, there is provided a kit for analyzing biomolecules, wherein the analysis single-stranded nucleic acid and the reference substance for analyzing biological significance of the biomolecules in the biosample are used.

According to another aspect of the present invention, there is provided an apparatus for analyzing biomolecules, wherein the biomolecules are analyzed by a method for analyzing biomolecules using an analysis single-stranded nucleic acid and a reference substance, and it has a system for analyzing biomolecules, including a sample treating device for preparing biomolecules in the biosample and an amplification device composed a module for preparing and amplifying a biomolecule-single-stranded nucleic acid complex and a module for analyzing the amplified product.

Advantageous Effects

With a reference substance and a nucleic acid chip according to the present invention, and a method for analyzing biomolecules in a biosample composed of two or more biomolecules using the same, it is possible to generate profiles of biomolecules contained in biosamples including microorganisms, cells, and proteins using a significantly simple, cheap, and efficient method and apparatus based on high throughput screening, and thus, the reference substance, the nucleic acid chip, and the method and the apparatus for analyzing biomolecules may be applied as useful tools for analyzing biological significance of the biomolecules in various fields including medicine, veterinary science, environmental engineering, food engineering, agriculture, and the like.

Further, with an external reference substance and a biochip according to the present invention, and a method for analyzing biomolecules using the same, it is possible to generate profiles of biomolecules contained in biosamples including microorganisms, cells, and proteins using a significantly simple, cheap, and efficient method based on high throughput screening, and thus, the external reference substance, the biochip, and the method for analyzing biomolecules may be applied as useful tools for analyzing biological significance of the biomolecules in various fields including medicine, veterinary science, environmental engineering, food engineering, agriculture, and the like.

In addition, with the external reference substance and the biochip according to the present invention, and the method for analyzing biomolecules using the same, during the analysis of biological significance of the biomolecules, it is possible to detect biological functions of unknown biomolecules, to determine and identify structures thereof, and to select single-stranded nucleic acids specifically binding to the biomolecules. Thus, the external reference substance and the biochip according to the present invention, and the method for analyzing biomolecules may be used as tools for accurately understanding the functions of the biomolecules using the selected single-stranded nucleic acids.

Furthermore, with the external reference substance and the biochip according to the present invention, and the method for analyzing biomolecules using the same, biomolecules that can serve as diagnostic markers, can be used to monitor therapeutic results, can play important roles in the outbreak or the progressions of diseases, are related to disease sensitivity, and can become target molecules for novel drug development, and the like, may be efficiently identified by a significantly cheap and simple method by analyzing the profile of the biomolecules medically associated with diseases.

BEST MODE

Figure 1:
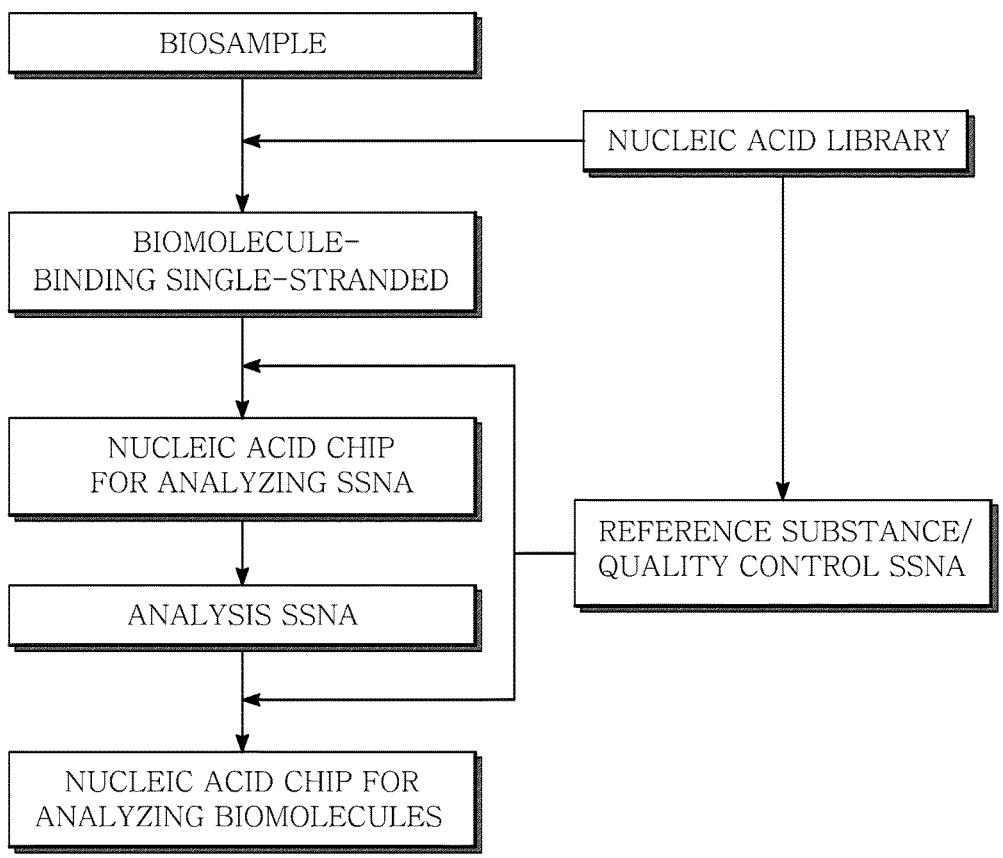
FIG. 1 is a view showing a series of processes of determining a biomolecule-binding single-stranded nucleic acid (SSNA) and a quality control single-stranded nucleic acid using biomolecules in a biosample composed of two or more biomolecules and a reference substance, determining an analysis single-stranded nucleic acid using a nucleic acid chip prepared based on base sequences of the single-stranded nucleic acids, and analyzing biological significance of the biomolecules in the biosample using a nucleic acid chip prepared using the analysis single-stranded nucleic acid and the quality control single-stranded nucleic acid.

Reference will now be made in greater detail to an exemplary embodiment of the present invention, an example of which is illustrated in the accompanying drawings. Wherever possible, the same reference numerals will be used throughout the drawings and the description to refer to the same or like parts.

The present invention provides a method for preparing an external reference substance and a biochip used to generate binding information on ligands and biomolecules; and a method for analyzing biomolecules using the same, and the external reference substance and the biochip according to the present invention may be used to analyze biological significance of biomolecules contained in a biosample.

Definitions of terms used herein are as follows. That is, the external reference substance, which is an external molecule that is not contained in a biosample to be analyzed, may be used in quality control and quantitative analysis of the biochip.

A capture probe is a molecule having information on ligands binding to biomolecules and the external reference substance, and is affixed onto the biochip.

A target probe, which is a molecule binding to the capture probe, is a mixture of an analysis target probe and a comparison target probe, or the target probe is composed of the analysis target probe. The analysis target probe may be an analysis target probe derived from a ligand binding to a biomolecule in an analysis biosample, and the comparison target probe may be a comparison target probe derived from a ligand binding to a biomolecule in a comparison biosample or artificially derived or artificially prepared from a pool of ligands binding to the biomolecule and external reference substance. Preferably, the target probe is composed of the analysis target probe and the comparison target probe.

A marker target probe, which is a molecule derived from a ligand binding to a capture probe corresponding to a marker molecule and binding to the external reference substance, may be divided into an analysis marker target probe and a comparison marker target probe depending on purpose of use.

Binding information may mean a profile composed of spots corresponding to capture probes configuring the biochip, or a fluorescence intensity of each of the spots.

A method for preparing an external reference substance and a biochip according to the present invention includes: a first step of determining biomolecules that are not contained in a biosample to be analyzed and preparing external reference substances using the determined external biomolecules; a second step of determining ligands binding to biomolecules and the external reference substances; a third step of determining a ligand for analyzing biological significance; and a fourth step of synthesizing a capture probe using information on the determined ligand to affix the capture probe onto a substrate.

The method for preparing an external reference substance according to the present invention is as follows. In the case of examining a biosample using a biochip, for example, transcripts, proteomes, or the like, may be examined. In the case of analyzing the transcripts, glyceraldehyde 3-phosphate dehydrogenase (GAPDH), actin mRNA, or the like, which is an internal marker, has been used for quality control, but there is no internal marker clearly used for quantitative analysis. Further, in the case of analyzing the proteome, there is no useful internal marker. Therefore, in the case of analyzing the proteomes, there are many difficulties in quality control and quantitative analysis. Therefore, the present invention is intended to provide a quality control method and a quantitative analysis method capable of being usefully used to analyze a biosample using an external reference substance.

The external reference substance is a substance (or a molecule) that is not contained in the biosample to be analyzed, and in the case of analyzing a human-derived biosample, for example, a plant-specific biomolecule may be used as a biomolecule that is not contained in the human-derived biosample. Currently, the human genome project and the *Arabidopsis thaliana* genome project (*Arabidopsis thaliana* is a kind of plant) were completed, and plant-specific proteins were reported. According to the present invention, in the case of analyzing the human-derived biosample, the plant-specific protein may be used as the external reference substance.

Further, the ligands binding to the biomolecules according to the present invention are as follows.

Examples of the ligands binding to the biomolecules and the external reference substance may include antibodies, peptides, single-stranded nucleic acids, aptamers, and the like.

In the case in which an aptamer (a single-stranded nucleic acid binding to a biomolecule in a three-dimensional structure) is used as a ligand binding to the biomolecules contained in a biosample, biomolecule-binding single-stranded nucleic acids may be determined using a reverse-SELEX method (see Korean Patent No. 10-0923048) of reacting the biosample containing the biomolecules with random single-stranded nucleic acids having random base sequences to determine the biomolecule-binding single-stranded nucleic acids binding to the biomolecules, and a ligand binding to the external reference substance may be determined using a SELEX method. In the present invention, the aptamer is referred to as the analysis single-stranded nucleic acid, the biomolecule-binding single-stranded nucleic acid, or the like.

Further, a method for preparing a biochip for analyzing biological significance according to the present invention may include affixing capture probes synthesized using at least one base sequence selected from base sequences of determined biomolecule-binding single-stranded nucleic acids and the external reference substance-binding single-stranded nucleic acid and base sequences complementary thereto onto the substrate.

A method for determining a ligand having biological significance by using a biochip according to the present invention includes: preparing the biochip; reacting biomolecule-binding single-stranded nucleic acids with biomolecules in a biosample to form biomolecule-single-stranded nucleic acid complexes, and separating the biomolecule-single-stranded nucleic acid complexes; separating single-stranded nucleic acids from the separated biomolecule-single-stranded nucleic acid complexes, and amplifying and labeling the separated single-stranded nucleic acids to prepare analysis target probes; reacting mixed target probes of the labeled analysis target probes and comparison target probes with capture probes of the biochip to obtain binding information through the labeling; and comparing the obtained profile and pre-secured data on binding information to analyze biological significance of the biomolecules.

Figure 16:
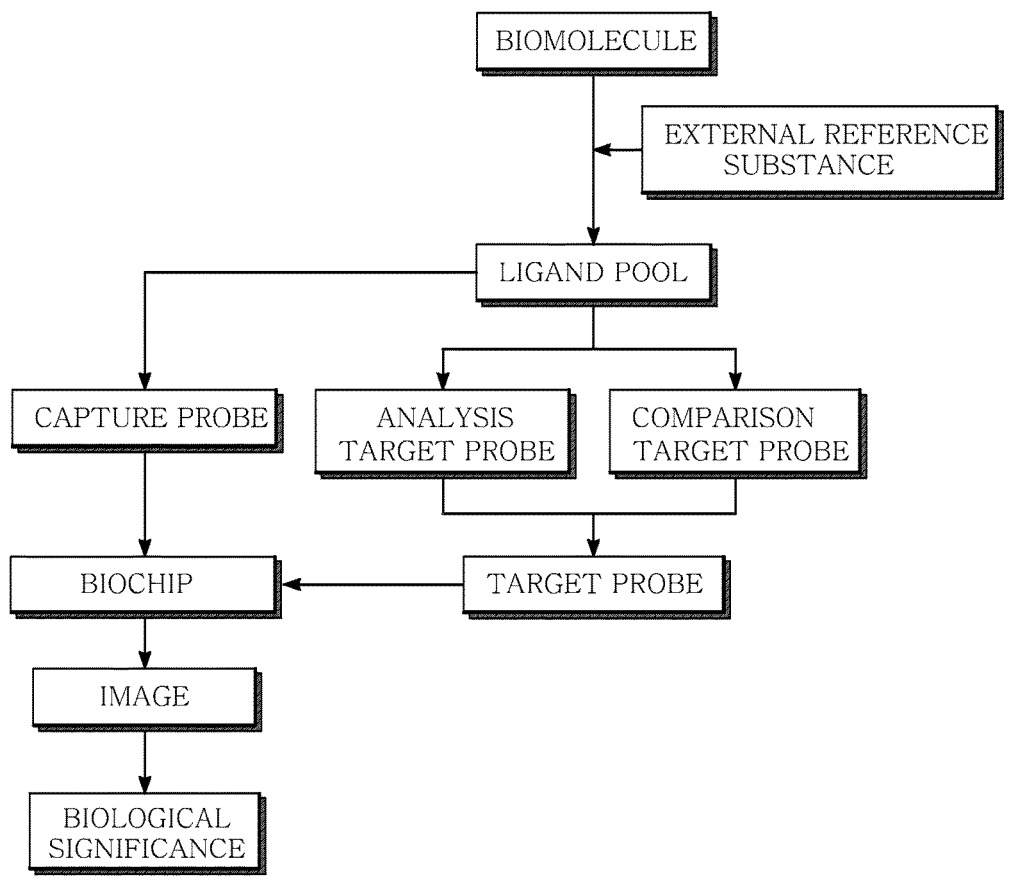
FIG. 16 is a schematic view showing a process of generating biological significance using an external reference substance and a biochip according to the present invention.
Figure 17:
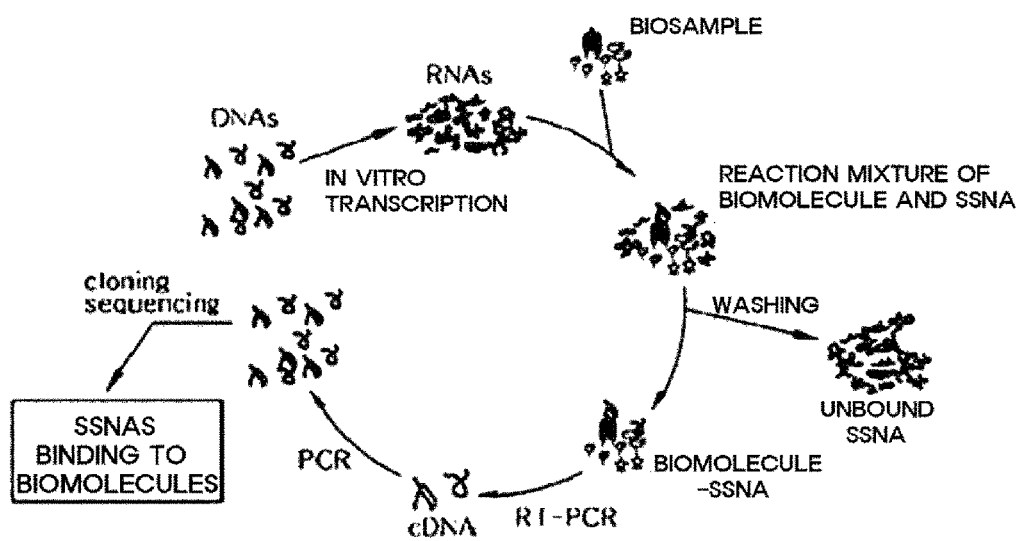
FIG. 17 is a schematic view showing a process of determining biomolecule-binding single-stranded nucleic acids associated with a method for preparing a biochip according to the present invention.

FIG. 16 is a mimetic view showing a process of generating biological significance using the external reference substance and the biochip according to the present invention.

The basic principle of the external reference substance and the biochip, and method for analyzing biomolecules using the same, according to the present invention will be described below. After affixing the capture probes including base sequence information on single-stranded nucleic acids binding to the biomolecules and the external reference substances onto the biochip and reacting biomolecules to be tested with single-stranded nucleic acids binding thereto to form biomolecule-single-stranded nucleic acid complexes, a binding profile of the capture probes of the biochip is obtained by reacting a target probe with the capture probes, wherein in the target probe, analysis target probes prepared from the complexes and a comparison target probe are mixed with each other, and characteristic of the binding profile are analyzed, such that binding profile characteristics with respect to the single-stranded nucleic acids binding to the biomolecules may be analyzed. Therefore, when the target probe having information on biomolecule-binding single-stranded nucleic acids is captured by complementary binding of the capture probes of the biochip, since the analysis target probes prepared through a process of amplifying the single-stranded nucleic acids separated from the biomolecule-single-stranded nucleic acid complexes are also produced in a state in which they include information identical or similar to profile information of the single-stranded nucleic acids of the complexes, at the time of analyzing the biomolecule, even though the target probes are analyzed using the capture probes of the biochip according to the present invention, the desired object may be achieved.

Further, in the obtaining of the binding information so as to recognize information on the biomolecules, the binding information may be generated by adding different amounts of external molecules configuring the external reference substances to the biosample to prepare the analysis target probe, or mixing different amounts of analysis marker target probes having information of ligands binding to the external molecules configuring the external reference substances with the analysis target probes to prepare the target probe. The comparison target probe may be prepared from a pool consisting of the ligands binding to biomolecules and ligands binding to external reference substances.

In the case of analyzing biomolecules using the biochip according to the present invention, related data on binding information are accumulated, and a specific single-stranded nucleic acid contributing to analysis of biological significance of the biomolecule may be naturally found therefrom, such that single-strand nucleic acids useful for analyzing biomolecules may be found.

The biosample to which the biochip according to the present invention may be applied includes bacteria, fungi, viruses, cell lines, tissue, and the like, and biomolecules of which biological significance may be analyzed by the biochip according to the present invention includes one or more biomolecules selected from the group consisting of proteins, carbohydrates, lipids, polysaccharides, glycoproteins, hormones, receptors, antigens, antibodies, enzymes, and nucleotides.

The first step of the method for preparing a biochip according to the present invention is a step of determining target single-stranded nucleic acids binding to unknown biomolecules by reacting the biosample containing the biomolecules with single-stranded nucleic acids having random base sequences (hereinafter, referred to as 'random single-stranded nucleic acids').

Preferably, the determining of the single-stranded nucleic acid binding to the biomolecules contained in the biosample includes: reacting the biomolecules of the biosample with the random single-stranded nucleic acids to prepare the biomolecule-single-stranded nucleic acid complexes, washing the complexes, selecting biomolecule-single-stranded nucleic acid complexes having a binding affinity above a predetermined level on the basis of binding affinities between the single-stranded nucleic acids and the biomolecules, and separating and amplifying single-stranded nucleic acids from the selected complexes; and inserting the amplified single-stranded nucleic acids into a cloning vector to secure a single clone and determining a base sequence thereof to determine biomolecule-binding single-stranded nucleic acids.

Selection and amplification of the biomolecule-single-stranded complexes may be repeatedly performed several times, but since the biosample containing an unknown biomolecule is composed of a number of biomolecules and there are significant quantitative differences between the biomolecules, it is more preferable to prepare the biomolecule-binding single-stranded nucleic acids using a linear method of performing selection and amplification once and intensify a washing process, rather than a cyclic method of repeatedly performing selection and amplification of the single-stranded nucleic acids binding to the biomolecules.

The random single-stranded nucleic acids having the random base sequences may be prepared as random single-stranded RNAs through in vitro transcription after preparing double-stranded DNA using a single-stranded DNA oligonucleotide having the following random base sequence.

```
                                           (SEQ ID NO: 5)
5'-GGGAGAGCGGAAGCGTGCTGGGCC N40
CATAACCCAGAGGTCGATGGATCCCCCC-3'
```

Here, underlined base sequences are invariable regions and N40 means the presence of bases such as adenine (A), guanine (G), thymine (T), cytosine (C), and the like, at equal concentration at each position.

```
5'-GGGAGAGCGGAAGCGTGCTGGGCC-3'
and

5'-CATAACCCAGAGGTCGATGGATCCCCCC-3'
``` are identified as SEQ ID NO. 1 and 2 respectively.

A forward (FW) primer used in polymerase chain reaction (PCR) may form base-pairing with 5'-terminals of the underlined bases of the above base sequence, and include a promoter base sequence for RNA polymerase of bacteriophage T7.

A reverse (RE) primer used in PCR may form base pairing with 3'-terminals of the underlined bases of the above base sequence.

Preferably, in the method for preparing a biochip according to the present invention, the biomolecule-binding single-stranded nucleic acids are single-stranded RNAs including 2'-F-substituted pyrimidine, and are synthesized by in vitro transcription and purified to thereby be prepared.

The synthesized random single-stranded nucleic acids may be reacted with the biomolecules for 30 minutes by treating the biosample with the synthesized random single-stranded nucleic acids, for example, at a concentration of $10^{15}$ base sequences/L.

In the cases of the target single-stranded nucleic acids, *E. coli* clone may be secured by inserting a product obtained by reverse-transcription (RT)-PCR into a cloning vector, and a base sequence thereof may be determined.

In this case, it is ideal that a reaction temperature is lower than a temperature for performing SELEX, and preferably, a reaction is performed at a temperature of 20° C. to 37° C.

Generally, non-specific binding of the single-stranded nucleic acids binding to the biomolecules is prevented by treating excessive amounts of proteins and single-stranded nucleic acids, and preferably, yeast tRNA, salmon sperm DNA, or human placental DNA may be used.

In the second step of the method for preparing a biochip for determining biomolecule-binding single-stranded nucleic acid having biological significance, according to the present invention, capture probes are synthesized using at least one base sequence selected from base sequences of the single-stranded nucleic acids determined in the first step and the external reference substance-binding single-stranded nucleic acid, and the base sequences complementary thereto, and the synthesized capture probes are affixed onto the substrate, thereby preparing the biochip according to the present invention.

Since the capture probe is a core factor having a large influence on a degree of hybridization, it is significantly important to determine base sequence configuration thereof. Each of the capture probes affixed onto the biochip according to the present invention is composed of a characteristic base, and hybrids between capture single-stranded nucleic acids and target single-stranded nucleic acids need to maintain suitable Tm values. Therefore, a degree of hybridization of the hybrids must be enough so that they can maintain their signals without contamination with fluorescent-labeled target probes.

Therefore, the base sequences of the capture probes may be determined based on the base sequences of the biomolecule-binding single-stranded nucleic acids selected from the random single-stranded nucleic acids of the nucleic acid library in the first step and the base sequence of the external reference substance-binding single-stranded nucleic acid. In detail, the capture probe uses 40 nucleotides corresponding to a random portion of the nucleic acid library, or a part thereof, and in the case of using the part, an artificial base sequence may be added. Preferably, the capture probes may be single-stranded nucleic acids of oligonucleotides having a base sequence of 10 bp to 20 bp.

In the case of analyzing a biosample using the biochip, as the target probe, a double target probe or single target probe is used. Generally, in the case of analyzing transcripts, a biosample derived from a disease site is set as an analysis biosample, a biosample derived from a normal site is set as a comparison biosample, an analysis target probe is prepared from the former, a comparison target probe is prepared from the latter, and then the analysis target probe and the comparison target probe are mixed with each other to thereby be used as a target probe. However, when there is no suitable comparison biosample, a single target probe derived from an analysis biosample is used as a target probe.

Further, the comparison target probe according to the present invention, which is a nucleic acid having a base sequence complementary to the capture probe, may be a single-stranded nucleic acid synthesized from a pool of ligands binding the biomolecules and ligands binding to the external reference substance. Preferably, the comparison target probe may be single-stranded nucleic acids of oligonucleotides having a base sequence of 80 bp to 140 bp.

The marker target probe is derived from a ligand binding to an external molecule configuring the external reference substance, and may be divided into an analysis marker target probe and a comparison marker target probe. In the case of preparing the analysis marker target probe by mixing the external reference substances with the biosample, the analysis marker target probe may be prepared together with the analysis target probe in a process of preparing the analysis target probe. Alternatively, in the case of using the external reference substances without mixing with the biosample, the analysis marker target probe capable of binding to the capture probe of the external reference substance may be prepared, and a mixture of the analysis marker target probe and the analysis target probe may be used. The comparison market target probe may be prepared from a pool of the ligands binding to the biomolecules and ligands binding to the external reference substance.

As the target probe according to the present invention, preferably, a mixture of the analysis target probe including the marker target probe and the comparison target probe including the marker target probe may be used.

Further, in the method for preparing a biochip according to the present invention, as the substrate, a substrate made of an inorganic material such as glass, silicon, or the like, or a polymer material such as acrylic polymers, polyethylene terephthalate (PET), polycarbonate, polystyrene, polypropylene, or the like, may be used. Preferably, the substrate may be a slide glass made of glass. In this case, a substrate coated with an amine group, an aldehyde group, or the like, may be used. For example, the biochip is prepared by arranging and affixing capture probes in a constant order using an UltraGAPS™ Coated Slide (Corning Inc.), which is a gamma amino propyl silane (GAPS)-coated glass slide.

In the method for preparing a biochip according to the present invention, a microarrayer system may be used, and each of the capture probes is dissolved in buffer to adjust a concentration. At this time, a humidity of 70%-80% is maintained inside the arrayer system while spotting is performed. After being kept in a humidified chamber, the spotted slides are baked in a UV crosslinker.

As described above, the biochip according to the present invention is stored in a state in which, after fixing the capture probes to the glass slide using a method widely known in the art and directly drying the slide by centrifugation, light is blocked before the biochip is used.

A biochip on which the capture probes are regularly arranged may be prepared using various methods known in the art (M. schena; DNA microarray; a practical approach, Oxford, 1999).

As long as the biochip according to the present invention may analyze biological significance of an unknown biomolecule with equal or similar accuracy, in view of manufacturing cost of the biochip and analysis efficiency, it is preferable to reduce the number of capture probes affixed onto the biochip.

For this reason, the method for preparing a biochip according to the present invention may further include reducing the number of capture probes to be affixed onto the biochip according to the present invention by analyzing a degree of contribution of each of the capture probes to analyzing biological significance of an unknown biomolecule and selecting the capture probes on the basis of the analyzed degree of contribution in a range in which the biological significance of the biomolecule may be analyzed.

Further, the present invention provides a reference substance and a nucleic acid chip for generating binding information on biomolecules in a biosample composed of two or more biomolecules and analysis single-stranded nucleic acids while performing internal quality control, a method for preparing the same, and a method and an apparatus for analyzing biomolecules using the same. The reference substance and the nucleic acid chip according to the present invention are used to analyze biological significance of the biomolecules contained in the biosample.

The nucleic acid chip indicates a supporter onto which a nucleic acid ligand is affixed in order to simultaneously analyzing one or more substances. Preferably, the supporter may be a solid glass or nylon substrate. The nucleic acid chip is produced in a form of a two-dimensional probe matrix manufactured on the solid glass or nylon substrate. It is significantly preferable to perform analysis for as many as possible characteristics in a single nucleic acid chip. Therefore, there is a need to significantly increase a density and an amount of the probe in the single substrate. In general, a microarray having probe fixation sites smaller than 500 nm (that is, having a density larger than 400 probes/$cm^2$) is referred to as a high-density microarray, and the other microarrays are referred to as "low-density" microarrays. In general, the nucleic acid chip is used to get information on a nucleic acid in an unknown sample through hybridization of an unknown nucleic acid sample with an already known nucleic acid fixed by arranging nucleic acids having various base sequences (hundreds to hundreds of thousands) in a small space. A nucleic acid microarray has an advantage in that it may simultaneously detect at least hundreds or more base sequence sites within a short time while replacing an existing southern blot method, northern blot method, mutation analysis method, or the like.

In general, a reference substance is an internal quality control substance for comparison at the time of qualitative and quantitative analysis, various tests, examinations, and in the present invention, the reference substance means a substance for internal quality control at the time of qualitative and quantitative analysis in analyzing the biomolecules in the biosample composed of two or more biomolecules to be analyzed using the analysis single-stranded nucleic acid. It is ideal that the reference substance is a substance constantly present in a sample to be analyzed at a predetermined amount. Otherwise, an external substance, a substance that is not contained in the sample, may be used. Preferably, in the case in which the sample to be analyzed is a biosample, the reference substance may be composed of external biomolecules that are not contained in the biosample. Quality control means internal quality control of analyzing a group of test results obtained at every time measurement to control precision of measured values without using external standard such as a control sample.

In the present invention, a single-stranded nucleic acid that has a base sequence of a single-stranded nucleic acid secured and determined by reacting biomolecules in a biosample composed of two or more biomolecules with a nucleic acid library composed of random single-stranded nucleic acids having random base sequences, and of which a stable secondary structure will be predicted is referred to as a binding single-stranded nucleic acid, and a single-stranded nucleic acid selected using the profile secured in order to analyze biological significance using a nucleic acid chip prepared based on the binding single-stranded nucleic acid is referred to as an analysis single-stranded nucleic acid. Further, a single-stranded nucleic acid determined for quality control as a single-stranded nucleic acid binding to the reference substance is referred to as a quality control single-stranded nucleic acid. All of these single-stranded nucleic acids are aptamers.

In the present invention, the term "aptamer" means a small (20 to 60 nucleotides) single-stranded nucleic acid (DNA or RNA) fragment capable of binding to various kinds of receptors from a low molecular compound to proteins with high affinity and specificity. Development of the aptamer is performed in a test tube by SELEX. SELEX, which is the abbreviation for 'systematic evolution of ligands by exponential enrichment', was initially developed in 1990 (Tuerk, C. and Gold, L., 1990, Systematic evolution of ligands by exponential enrichment: RNA ligands to bacteriophage T4 DNA polymerase. Science 249 (4968), 505-510; Ellington, A. D. and Szostak, J. W., 1990, In vitro selection of RNA molecules that bind specific ligands. Nature 346 (6287), 818-822). A nucleic acid aptamer having a high binding affinity to a specific molecule may be obtained using SELEX. The aptamer is considered as a nucleic acid molecule having characteristics similar to those of an antibody in that it has a high binding affinity and selectivity to a receptor at a level of nano moles to pica moles. The aptamer is selected in a test tube through SELEX. The central principle of SELEX is significantly similar to a concept of evolution that among a large number of randomly existing individuals, only individuals having a specific characteristic can survive, and the individuals that survived as described above gradually account for a large portion in the group, thereby dominating the group. However, an individual in SELEX is a single-stranded nucleic acid, and a selective pressure is a binding affinity to a specific receptor. Therefore, there is a need to form a nucleic acid library having a large number of random sequences, a fraction process capable of selecting individuals having a high binding affinity to a specific receptor expected to be present in this library is required, and an amplification step of amplifying the selected aptamer to increase a ratio thereof in the pool of nucleic acids so as to perform selection in next round is required. A specific method, reagents/materials, and the like, for aptamers in SELEX were known in the art (Marshall, K. A. and Ellington, A. D., 2000, In vitro selection of RNA aptamers. Methods Enzymol 318, 193-214; Fitzwater, T. and Polisky, B., 1996, A SELEX primer. Methods Enzymol 267, 275-301). Further, the present inventor suggested a method for selecting a single-stranded nucleic acid specifically binding to each biomolecule by reacting the biomolecules in a biosample composed of two or more biomolecules with a nucleic acid library composed of random single-stranded nucleic acids having random base sequences (Korean Patent No. 10-0923048).

The present invention provides a method for analyzing a biomolecule by an analysis single-stranded nucleic acid, wherein a quality control reference substance for analyzing an analysis single-stranded nucleic acid binding to biomolecules in a biosample composed of two or more biomolecules is used, and the binding single-stranded nucleic acid is selected from a nucleic acid library composed of random single-stranded nucleic acids having random base sequences, whereby internal quality control is performed by analyzing a quality control single-stranded nucleic acid using a nucleic acid analysis method.

Further, the present inventor suggested a method of analyzing an aptamer in a biomolecule-aptamer complex produced by reacting a biomolecule in a biosample with the aptamer using a nucleic acid analysis method to analyze the biomolecule, which is a receptor (Korean Patent No. 10-0670799). The nucleic acid analysis method for analyzing the aptamer in the biomolecule-aptamer complex in the biosample may be performed using polymerase chain reaction (PCR), ligase chain reaction (LCR), strand displacement amplification (SDA), transcription-mediated amplification (TMA), branched DNA, invader assay, rolling circle amplification (RCA), and the like. Preferably, an amplification product produced by PCR using a single-stranded nucleic acid in the biomolecule-single-stranded nucleic acid complex as a template may be additionally analyzed.

Further, the present invention provides the method for selecting a biomolecule analysis single-stranded nucleic acid, wherein the quality control reference substance is a biomolecule that is not contained in the biosample.

FIG. 1 shows a series of processes of reacting the biomolecule in the biosample and the reference substance with random single-stranded nucleic acids having random base sequences to determine the binding single-stranded nucleic acid and the quality control single-stranded nucleic acid, and analyzing biological significance of the biomolecule in the biosample using a nucleic acid chip prepared using base sequences of the analysis single-stranded nucleic acid and the quality control single-stranded nucleic acid.

Representative examples of the biosample tested using the nucleic acid chip may include transcripts, proteome, and the like. In the case of analyzing a dead body, glyceraldehyde 3-phosphate dehydrogenase (GAPDH), β-actin mRNA, or the like, which is expressed in a constant amount in almost every tissue, has been used for internal quality control as a reference substance, but there is no reference substance for accurate quantitative analysis. Therefore, accuracy of quantitative analysis is dependent on external quality control.

In addition, as a method for selecting a ligand binding to proteins in a biosample composed of two or more proteins, there are reverse-SELEX suggested by the present inventor (Korean Patent No. 10-0923048) and cell-SELEX (Homann, M. and Goringer, H. U., 1999, Nucleic Acids Res. 27 (9), 2006-2014). The present invention is intended to provide a quality control reference substance for efficiently selecting a ligand binding to a biomolecule in a biosample containing two or more biomolecules using reverse-SELEX.

Further, in the case of analyzing proteome, since there is no useful reference substance capable of being used in qualitative and quantitative analysis, there are a lot of difficulties in quality control and quantitative analysis for analyzing the proteome. Therefore, the present invention is intended to provide a useful internal quality control and quantitative analysis method for analyzing a sample using a reference substance.

Preferably, in the case of analyzing a human-derived biosample, as the reference substance according to the present invention, a plant-specific biomolecule, which is a biomolecule that is not contained in the human-derived biosample, may be used, similarly to the external reference substance as described above. Currently, the human genome project and the *Arabidopsis thaliana* genome project (*Arabidopsis thaliana* is a kind of plant) were completed, and plant-specific proteins were reported. In the present invention, as a reference substance for analyzing a human-derived biosample, the plant-specific protein may be used.

Substances binding to the biomolecules contained in the biosample and the reference substances may include antibodies, peptides, single-stranded nucleic acids, and the like, and preferably, the substances may be the single-stranded nucleic acids.

The present invention provides a method for selecting a biomolecule analysis single-stranded nucleic acid so as to generate binding profiles between biomolecules and binding single-stranded nucleic acids using a biosample, a reference substance, a binding single-stranded nucleic acid, a quality control single-stranded nucleic acid, and a nucleic acid chip, in order to select an analysis single-stranded nucleic acid for analyzing biological significance of biomolecules, the method including: determining a biomolecule that is not contained in the biosample and preparing the quality control single-stranded nucleic acid from the determined external biomolecules; preparing the binding single-stranded nucleic acids from the biomolecules contained in the biosample; and preparing a supporter onto which capture probes synthesized using base sequences of the quality control single-stranded nucleic acid and the binding single-stranded nucleic acid are affixed.

Figure 2:
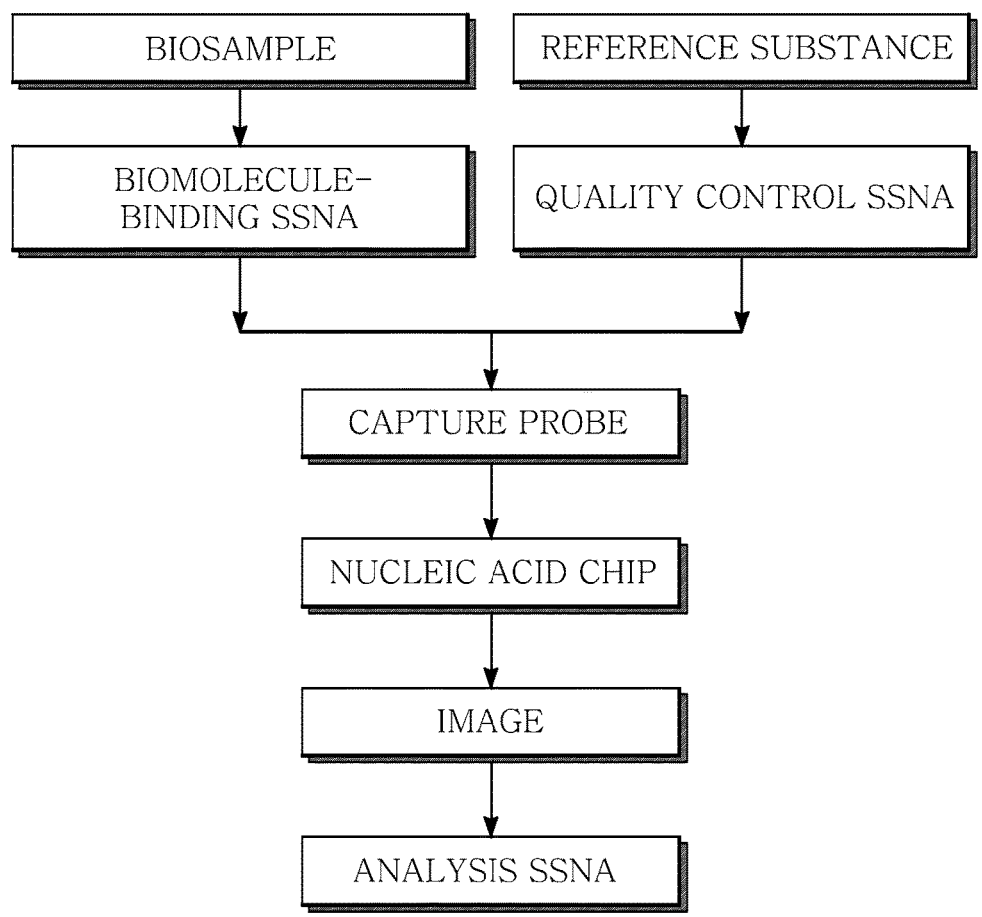
FIG. 2 is a view showing a series of processes of preparing a nucleic acid chip using the biomolecule-binding single-stranded nucleic acid and the quality control single-stranded nucleic acid to determine the analysis single-stranded nucleic acid.

FIG. 2 shows a series of processes of selecting the binding single-stranded nucleic acid of the biomolecule in the biosample and the quality control single-stranded nucleic acid to prepare a nucleic acid chip, and analyzing biological significance of the biomolecules in the biosample.

A method for determining the quality control single-stranded nucleic acid among single-stranded nucleic acids binding to the reference substances according to the present invention may be performed by a standard SELEX method (Tuerk C. and Gold L., 1990, Science, 249; 505-510) of reacting the reference substance and random single-stranded nucleic acids having random base sequences to separate the reference substances and the single-stranded nucleic acid and repeatedly performing this series of selection and amplification to select the single-stranded nucleic acid binding to the reference substance.

Further, in a method for selecting a single-stranded nucleic acid binding to the biomolecule present in a biosample composed of two or more biomolecules according to the present invention, a reverse-SELEX method (Korean Patent No. 10-0923048) of reacting the biosample containing the biomolecules with random single-stranded nucleic acids having random base sequences to determine biomolecule-binding single-stranded nucleic acids binding to the biomolecules may be used.

A method for preparing the binding single-stranded nucleic acids provided in the present invention, which is the same as the method for selecting a single-stranded nucleic acid binding to the biomolecule contained in the biosample as described above, may include: selecting biomolecule-single-stranded nucleic acid complexes in a reaction solution obtained by reacting the biomolecules with random single-stranded nucleic acids having random base sequences; separating the single-stranded nucleic acids from the complexes and amplifying the separated single-stranded nucleic acids to prepare single-stranded DNAs, and inserting the single-stranded DNAs into a cloning vector to secure a single clone and preparing the binding single-stranded nucleic acids through base sequencing of the single-stranded nucleic acid, thereby making it possible to select the biomolecule analysis single-stranded nucleic acid.

The present invention provides a method for selecting a biomolecule analysis single-stranded nucleic acid, wherein in the selecting of the biomolecule-single-stranded nucleic acid complexes, the biomolecule-single-stranded nucleic acid complexes in the reaction solution are washed and biomolecule-single-stranded nucleic acid complexes having a binding affinity above a predetermined level on the basis of binding affinities between the single-stranded nucleic acids and the biomolecules are selected.

The present invention provides the method for selecting a biomolecule analysis single-stranded nucleic acid, wherein in the selecting of the biomolecule-single-stranded nucleic acid complexes, the biomolecule-single-stranded nucleic acid complexes are selected by performing capillary electrophoresis on the reaction solution.

The present invention provides the method for selecting a biomolecule analysis single-stranded nucleic acid, wherein in the selecting of the biomolecule-single-stranded nucleic acid complexes, the biomolecule-single-stranded nucleic acid complexes are selected by treating the reaction solution with a structure of nitrocellulose and nylon.

The present invention provides the method for selecting a biomolecule analysis single-stranded nucleic acid, wherein selection and amplification of the biomolecule-single-stranded nucleic acid complexes are repeatedly performed several times.

In the present invention, the biomolecule-single-stranded nucleic acid complexes may be selected by the method of washing the formed biomolecule-single-stranded nucleic acid complexes and selecting biomolecule-single-stranded nucleic acid complexes having a binding affinity above a predetermined level on the basis of binding affinities between the single-stranded nucleic acids and the biomolecules, the method of performing electrophoresis on the reaction solution to select the biomolecule-single-stranded nucleic acid complexes, the method of treating the reaction solution with the structure of nitrocellulose and nylon to select the biomolecule-single-stranded nucleic acid complexes, and the like.

Products obtained by performing reverse transcription (RT)-PCR on the single-stranded nucleic acids separated from the biomolecule-single-stranded nucleic acid complexes are inserted into cloning vectors to secure E. coli clones, and base sequences of the single-stranded nucleic acids may be determined.

The present invention provides the method for selecting a biomolecule analysis single-stranded nucleic acid, wherein the supporter onto which the capture probe is affixed is selected from a glass slide, a sensing surface of a biosensor, beads, nanoparticles, and the like.

The present invention provides the method for selecting a biomolecule analysis single-stranded nucleic acid, wherein the capture probe is composed of and synthesized from at least one base sequence selected from base sequences of the binding single-stranded nucleic acids and the quality control single-stranded nucleic acid and base sequences complementary thereto.

The present invention provides the method for selecting a biomolecule analysis single-stranded nucleic acid, wherein the generating of the binding profiles between the biomolecules in the biosample composed of two or more biomolecules and binding single-stranded nucleic acids includes: preparing analysis target probes containing a labeling substance from the reference substance, the biosample, the quality control single-stranded nucleic acid, and the binding single-stranded nucleic acids; preparing comparison target probes containing a labeling substance by mixing and amplifying the binding single-stranded nucleic acids corresponding to the capture probes and the quality control single-stranded nucleic acid; preparing target probes by mixing the analysis target probes and the comparison target probes with each other; and generating the binding profiles by performing a hybridization reaction between the target probes and the capture probes on the supporter.

The present invention provides the method for selecting a biomolecule analysis single-stranded nucleic acid, wherein the preparing of the analysis target probes includes: preparing an analysis sample obtained by adding a reference substance I composed of different amounts of reference substances to the biosample; separating biomolecule-single-stranded nucleic acid complexes and reference substance-single-stranded nucleic acid complexes formed by reacting the analysis sample with the single-stranded nucleic acids composed of the binding single-stranded nucleic acids and the quality control single-stranded nucleic acid; and preparing the analysis target probes by separating the single-stranded nucleic acids from the separated complexes and amplifying and labeling the separated single-stranded nucleic acids.

The present invention provides the method for selecting a biomolecule analysis single-stranded nucleic acid, wherein the preparing of the analysis target probe includes: separating single-stranded nucleic acids from the biomolecule-single-stranded nucleic acid complexes formed by reacting the biosample with the binding single-stranded nucleic acids; and preparing the analysis target probes by mixing a reference substance II composed of different amounts of quality control single-stranded nucleic acids with the separated single-stranded nucleic acids and performing amplification and labeling thereon.

The present invention provides a method for selecting a biomolecule analysis single-stranded nucleic acid, in order to analyze biological significance of the biomolecules, wherein the method further includes reducing the number of capture probes to be affixed onto the biochip by selecting the capture probes on the basis of the degree of contribution of the capture probes in a range in which the biological significance of the biomolecule may be analyzed.

The present invention provides a nucleic acid chip, wherein capture probes synthesized using base sequences of the binding single-stranded nucleic acids and quality control single-stranded nucleic acid are affixed onto a supporter of the nucleic acid, and the nucleic acid chip is used to generate binding information on the binding single-stranded nucleic acids and the quality control single-stranded nucleic acid for selecting the analysis single-stranded nucleic acid.

In a method for selecting an analysis single-stranded nucleic acid using the nucleic acid chip according to the present invention, the capture probes, which are molecules affixed onto the supporter, may be single-stranded nucleic acids binding to the biomolecules and the reference substance, or may be composed of one or more substances selected from substances having information on the single-stranded nucleic acids.

The binding information on the biomolecules in the biosample and the single-stranded nucleic acids indicates signals generated by complementary binding between the target probes prepared from the binding single-stranded nucleic acids and the capture probes. Preferably, the binding information means profiles composed of spots corresponding to the capture probes configuring the supporter, and preferably, fluorescence intensities as signals generated from the labeling substance in the binding single-stranded nucleic acid in the target probe binding to each of the capture probes configuring respective spots. The binding information is a combination of signals of the analysis target probe and the comparison target probe of the target probe. Ultimately, the binding information indicates a distribution state of the biomolecule-binding single-stranded nucleic acids in the biosample, and a distribution state of the biomolecules binding to the single-stranded nucleic acids may be deduced therefrom.

Further, in a nucleic acid chip for selecting an analysis single-stranded nucleic acid in order to analyze biological significance of biomolecules in the biosample according to the present invention, capture probes synthesized using at least one base sequence selected from the base sequences of the determined analysis single-stranded nucleic acid and the quality control single-stranded nucleic acid and base sequences complementary thereto, or synthesized using capture probes having base sequences forming a completely complementary binding with the base sequences of the biomolecule-binding single-stranded nucleic acids are affixed onto the supporter.

In addition, according to the present invention, the supporter onto which the capture probes may be affixed may be selected from a glass slide, a sensing surface of a bio sensor, beads, nanoparticles, and the like, and preferably, the supporter may be the glass slide.

A method for amplifying signals of amplification products binding to the capture probes may be selected depending on the kind of supporter.

As described above, the biochip according to the present invention is stored in a state in which, after affixing the capture probes onto the glass slide and directly drying the slide by centrifugation, light is blocked before the biochip is used.

A nucleic acid chip on which the capture probes are regularly arranged may be prepared using various methods known in the art (M. schena; DNA microarray; a practical approach, Oxford, 1999).

When a biosample is analyzed using a nucleic acid chip, generally, in the case of analyzing transcripts, a biosample derived from a disease site is set as an analysis biosample, a biosample derived from a normal site is set as a comparison biosample, an analysis target probe is prepared from the former, a comparison target probe is prepared from the latter, and then the analysis target probe and the comparison target probe are mixed with each other to thereby be used as a target probe. However, when there is no suitable comparison biosample, a single target probe derived from an analysis biosample may also be used as a target probe.

Preferably, the target probe may be single-stranded nucleic acids of oligonucleotides having a base sequence of 80 bp to 140 bp.

Further, in the present invention, the analysis target probe may be prepared using the following two methods: in one method, the analysis target probe may be prepared by mixing the reference substance I composed of different amounts of reference substances with the biosample, and in the other method, the analysis target probe may be prepared by mixing the reference substance II composed of different amounts of quality control single-stranded nucleic acids with the single-stranded nucleic acids separated from the biomolecule-single-stranded nucleic acid complexes.

The comparison target probe, which is a nucleic acid having a base sequence complementary to the capture probe, may be a single-stranded nucleic acid synthesized from a pool of single-stranded nucleic acids composed of the biomolecule-binding single-stranded nucleic acids and the quality control single-stranded nucleic acids.

For this reason, the analysis single-stranded nucleic acids useful for analyzing biomolecules may be found by analyzing a degree of contribution of each of the capture probes to analyzing biological significance of the biomolecules and selecting capture probes on the basis of the analyzed degree of contribution in a range in which the biological significance of the biomolecules may be analyzed.

The present invention provides a method for analyzing biomolecules, wherein the quality control reference substance for analyzing biomolecules in the biosample using the analysis single-stranded nucleic acid is used, and internal quality control is performed by analyzing the quality control single-stranded nucleic acid using a nucleic acid analysis method.

Further, the present invention provides a method for analyzing biomolecules, wherein analysis of the biomolecules in the biosample using the analysis single-stranded nucleic acid is performed by the nucleic acid analysis method.

Figure 3:
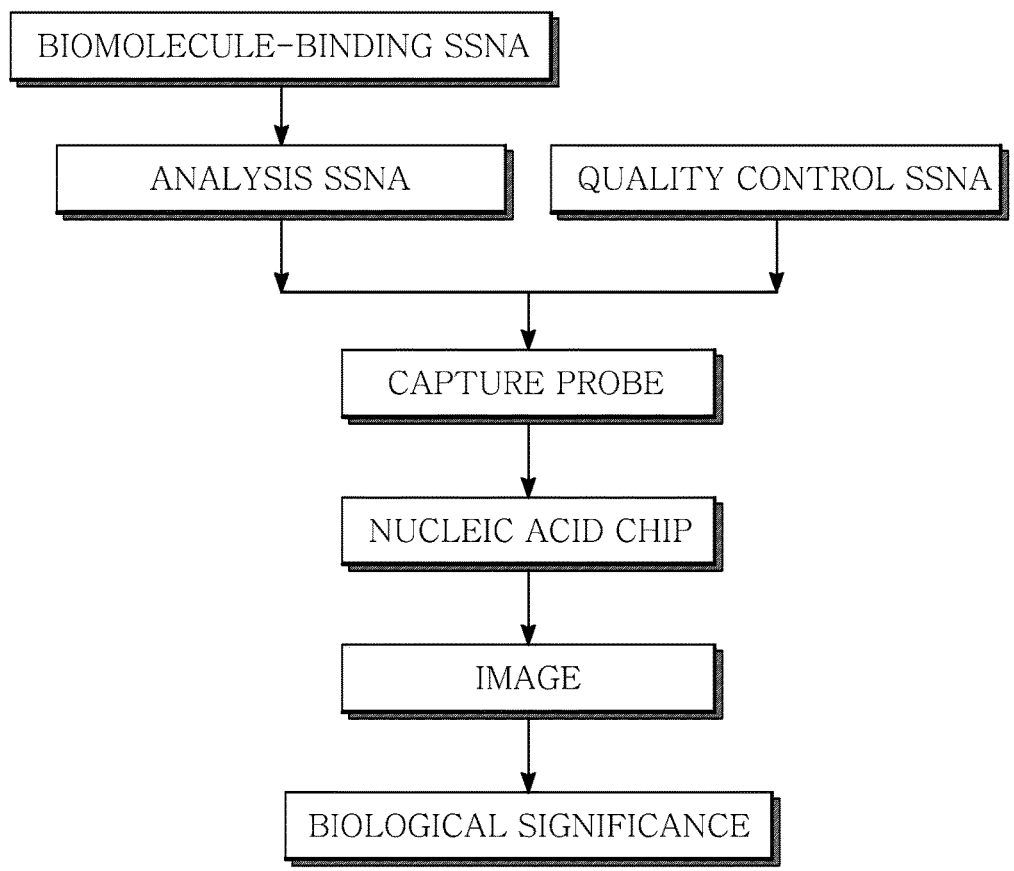
FIG. 3 is a view showing a series of processes of preparing a nucleic acid chip for analyzing biological significance of biomolecules in a biosample using the analysis single-stranded nucleic acid and the quality control single-stranded nucleic acid to generate a binding profile between the biomolecules in the biosample and the analysis single-stranded nucleic acid.

FIG. 3 shows a series of processes of preparing the nucleic acid chip for analyzing biological significance of biomolecules in a biosample using the analysis single-stranded nucleic acid and the quality control single-stranded nucleic acid to generate a binding profile between the biomolecules in the biosample and the analysis single-stranded nucleic acid.

The present inventor suggested a method for analyzing an aptamer in a biomolecule-aptamer complex produced by reacting a biomolecule in a biosample with the aptamer using a nucleic acid analysis method to analyze the biomolecule, which is a receptor (Korean Patent No. 10-0670799-0000). The nucleic acid analysis method for analyzing biomolecules in the biosample and the aptamer in the biomolecule-aptamer complex may be performed using polymerase chain reaction (PCR), ligase chain reaction (LCR), strand displacement amplification (SDA), transcription-mediated amplification (TMA), branched DNA, invader assay, rolling circle amplification (RCA), and the like. Preferably, an amplification product produced by PCR using a nucleic acid in the biomolecule-single-stranded nucleic acid complex as a template may be additionally analyzed.

Further, the present invention provides the method for analyzing biomolecules, wherein the quality control reference substance is a biomolecule that is not contained in the biosample.

The present invention provides the method for analyzing biomolecules, the method including: affixing the capture probes synthesized using base sequences of the analysis single-stranded nucleic acid and the quality control single-stranded nucleic acid onto a supporter; preparing a target probe containing a labeling substance from the reference substance, the biosample, the quality control single-stranded nucleic acid, and the analysis single-stranded nucleic acid; obtaining binding information by performing a hybridization reaction between the target probe and the capture probe on the supporter; and comparing the obtained binding information and pre-secured data on binding information to analyze biological significance of the biomolecules.

In addition, the present invention provides the method for analyzing biomolecules, wherein the preparing of the target probe includes: preparing an analysis target probe containing the labeling substance from the reference substance, the biosample, the quality control single-stranded nucleic acid, and the analysis single-stranded nucleic acid; preparing a comparison target probe containing the labeling substance by mixing and amplifying the analysis single-stranded nucleic acid corresponding to the capture probe and the quality control single-stranded nucleic acid; and preparing a target probe composed of the analysis target probe and the comparison target probe.

Figure 4:
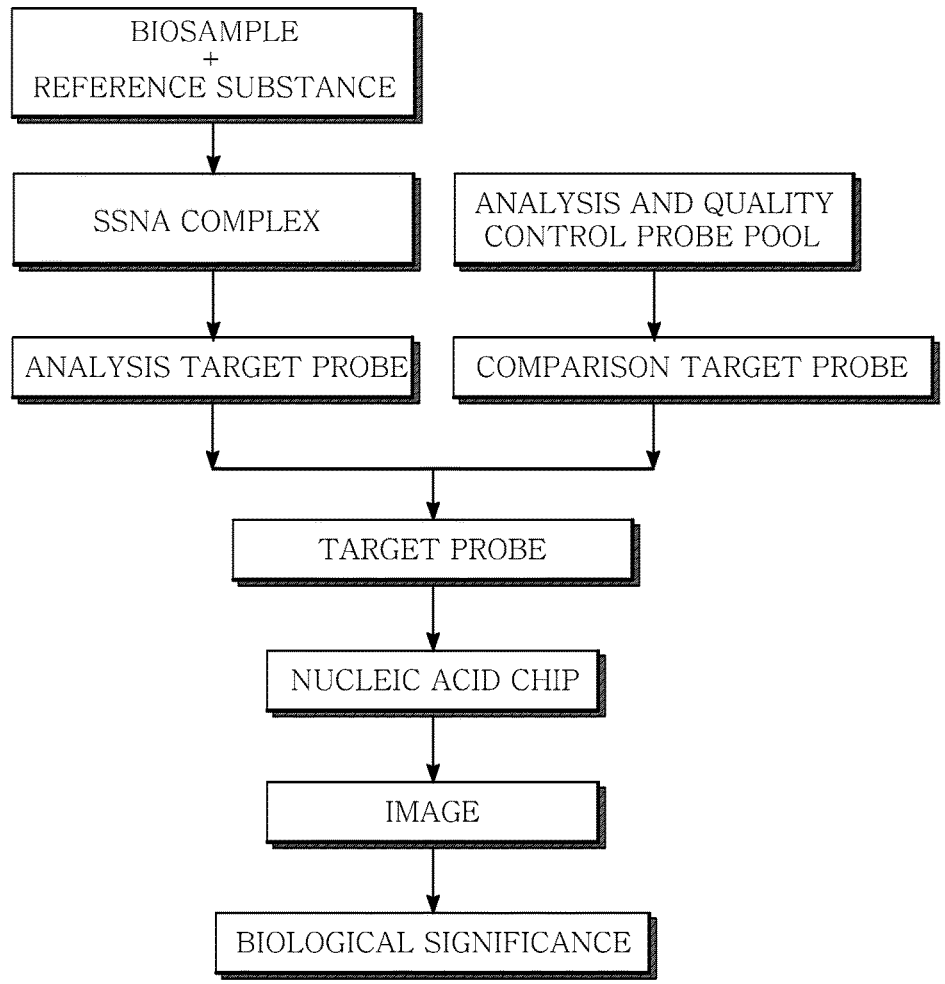
FIG. 4 is a view showing a series of processes of performing quality control using a reference substance I in a process of analyzing biological significance of biomolecules contained in a biosample using a nucleic acid chip prepared using an analysis single-stranded nucleic acid and a quality control single-stranded nucleic acid.
Figure 5:
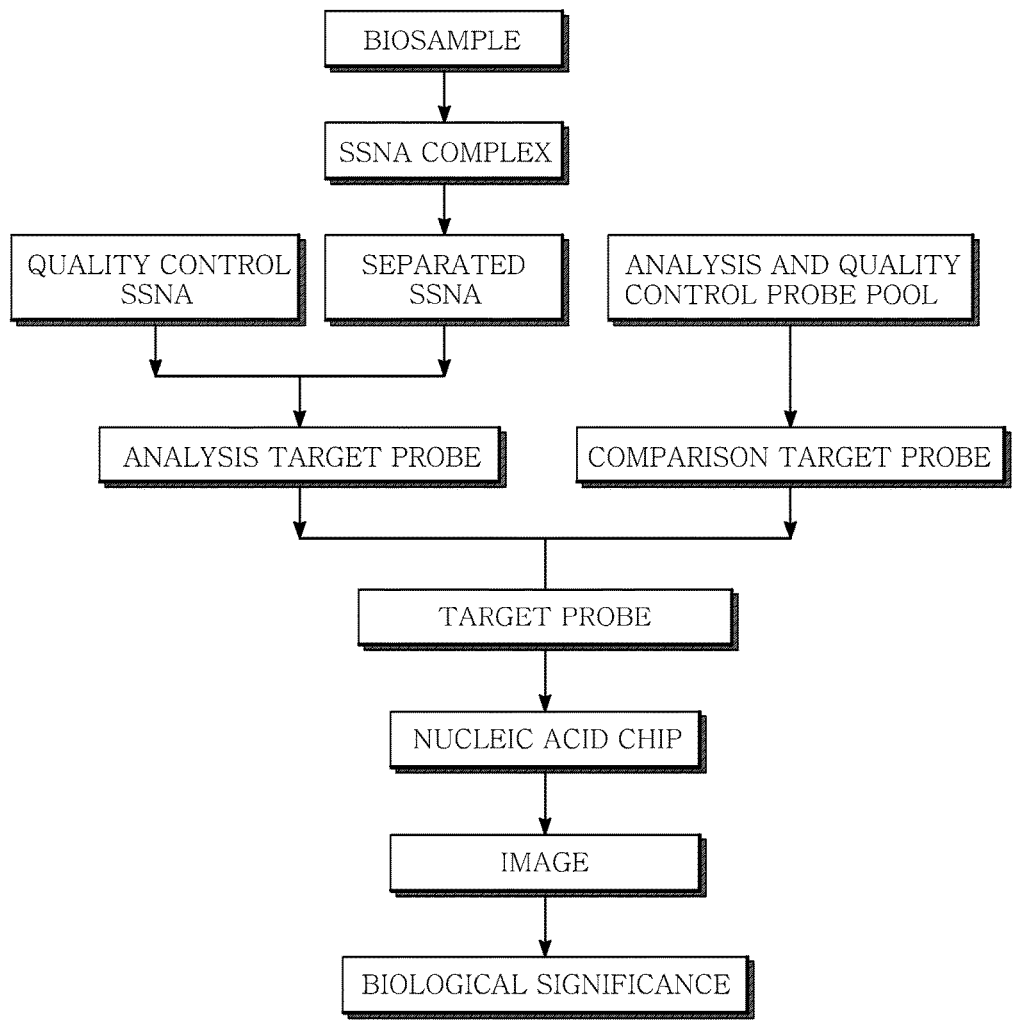
FIG. 5 is a view showing a series of processes of performing quality control using a reference substance II in a process of analyzing biological significance of biomolecules contained in a biosample using a nucleic acid chip prepared using an analysis single-stranded nucleic acid and a quality control single-stranded nucleic acid.

FIGS. 4 and 5 show a series of processes of performing analysis using the reference substance and the quality control single-stranded nucleic acid for quality control, in a process of preparing a nucleic acid chip using the analysis single-stranded nucleic acid and the quality control single-stranded nucleic acid to analyze biological significance of the biomolecules contained in the biosample.

The present invention provides the method for analyzing biomolecules, wherein the supporter onto which the capture probes are affixed may be selected from a glass slide, a sensing surface of a biosensor, beads, nanoparticles, and the like.

The present invention provides the method for analyzing biomolecules, wherein the capture probe is composed of base sequences forming completely complementary binding with base sequences of the analysis single-stranded nucleic acid and the quality control single-stranded nucleic acid.

Preferably, the capture probe may be composed of a base sequence forming complementary binding with the analysis single-stranded nucleic acid, wherein the analysis single-stranded nucleic acid is an aptamer selected from the binding single-stranded nucleic acids configuring the biosample and used for analyzing biological significance of the biomolecules in the biosample. Therefore, since the capture probe may form complementary binding with a base sequence of a specific analysis single-stranded nucleic acid in an amplification product obtained by performing PCR using the analysis single-stranded nucleic acid in the complex as a template, ultimately, a protein corresponding to a receptor may be quantitatively analyzed using a result obtained by analyzing the analysis single-stranded nucleic acid in the complex.

A method for amplifying signals of amplification products binding to the capture probes may be selected depending on the kind of supporter.

In a method for analyzing biological significance of biomolecules using the nucleic acid chip while performing internal quality control according to the present invention, capture probes, which are molecules affixed onto a supporter, may be single-stranded nucleic acids binding to the biomolecules and a reference substance or be composed of one or more substances selected from substances having information on the single-stranded nucleic acids.

The present invention provides the method for analyzing biomolecules, wherein a primer containing a labeling substance, for labeling and amplifying single-stranded nucleic acids separated from the biomolecule-single-stranded nucleic acid complex and the reference substance-single-stranded nucleic acid complex is used.

Further, in the present invention, a primer containing a labeling substance, for labeling and amplifying single-stranded nucleic acids separated from the biomolecule-single-stranded nucleic acid complex and the reference substance-single-stranded nucleic acid complex, and primer having a tag directing a specific single-stranded nucleic acid may be used.

The term "tag" means unique nucleotide sequences used to identify polynucleotides and/or track the origin of the polynucleotides in a reaction. A tag sequence may be present at the 5-terminal or 3-terminal of the primer. The base sequences of the capture probes may be variously changed in size and compositions; the following references provide guidance for selecting sets of capture probes appropriate for particular embodiments (U.S. Pat. No. 5,635,400; Brenner et al, 2000, PNAS., 97: 1665-1670; Shoemaker et al, 1996, Nature Genetics, 14: 450-456; EP Patent Publication No. 0799897A1; U.S. Pat. No. 5,981,179, and the like). In particular embodiments, the base sequence of the capture probe may have a length in a range of 4 to 36 nucleotides, 6 to 30 nucleotides, or 8 to 20 nucleotides.

The present invention provides the method for analyzing biomolecules, wherein the capture probe is composed of base sequences forming completely complementary binding with a base sequence of the tag directing the analysis single-stranded nucleic acid and the quality control single-stranded nucleic acid.

The capture probe may be prepared using a base sequence complementary to the tag, and since this capture probe may form completely complementary binding with the base sequence of the tag in a PCR product formed by performing PCR using an analysis single-stranded nucleic acid in the complex as a template, the PCR product may be analyzed, and the analysis single-stranded nucleic acid in the complex may be analyzed by analyzing signals of spots generated by the capture probe and the PCR product.

The comparison target probe, which is a nucleic acid having a base sequence complementary to the capture probe, may be a single-stranded nucleic acid synthesized from a pool of single-stranded nucleic acids composed of the biomolecule-binding single-stranded nucleic acids and the quality control single-stranded nucleic acids.

Generally, in the case of analyzing transcripts using a nucleic acid chip, a biosample derived from a disease site is set as an analysis biosample (experimental biosample), a biosample derived from a normal site is set as a comparison biosample (control biosample), an analysis target probe is prepared from the former, a comparison target probe is prepared from the latter, and then the analysis target probe and the comparison target probe are mixed with each other to thereby be used as a target probe. However, when there is no suitable comparison biosample, a single target probe derived from the analysis biosample may also be used as the target probe.

Further, in the present invention, the analysis target probe may be prepared using following two methods: In one method, the analysis target probe may be prepared by mixing the reference substance I composed of different amounts of reference substances with the biosample, and in the other method, the analysis target probe may be prepared by mixing the reference substance II composed of different amounts of quality control single-stranded nucleic acids with the single-stranded nucleic acids separated from the biomolecule-single-stranded nucleic acid complexes.

The present invention provides the method for analyzing biomolecules, wherein the preparing of the analysis target probe includes: preparing an analysis sample obtained by adding a reference substance I composed of different amounts of reference substances to the biosample; separating biomolecule-single-stranded nucleic acid complexes and reference substance-single-stranded nucleic acid complexes formed by reacting the analysis sample with single-stranded nucleic acids composed of the analysis single-stranded nucleic acids and the quality control single-stranded nucleic acid; and preparing the analysis target probe by separating the analysis single-stranded nucleic acids from the complexes and amplifying and labeling the separated analysis single-stranded nucleic acids.

The present invention provides a method for analyzing biomolecules, wherein the preparing of the analysis target probe includes: separating biomolecule-single-stranded nucleic acid complexes formed by reacting the biomolecules in the biosample with the analysis single-stranded nucleic acids; and mixing the reference substance II composed of different amounts of quality control single-stranded nucleic acids with the analysis single-stranded nucleic acid separated from the separated biomolecule-single-stranded nucleic acid complex and amplifying and labeling the mixture to prepare the labeled analysis target probe.

The present invention provides a method and an apparatus for analyzing biomolecules, wherein a nucleic acid chip is analyzed using a target probe prepared by mixing an analysis target probe and a comparison target probe with each other, the analysis target probe being prepared by reacting an analysis single-stranded nucleic acid with biomolecules in a biosample (experimental biosample) and a comparison target probe being prepared by reacting the analysis single-stranded nucleic acid with biomolecules in a biosample (control biosample).

A target probe derived from an analysis single-stranded nucleic acid binding to the biomolecule in the experimental biosample is referred to as the analysis target probe, and a target probe derived from an analysis single-stranded nucleic acid binding to the biomolecule in the control biosample or artificially prepared from a pool of analysis single-stranded nucleic acids binding to biomolecules and reference substances is referred to as the comparison target probe. Preferably, the target probe is composed of the analysis target probe and the comparison target probe.

The target probe, which is a molecule binding to the capture probe, may be composed of a mixture of the analysis target probe and the comparison target probe, or be composed of only the analysis target probe.

The present invention provides a method and an apparatus for analyzing biomolecules, wherein as the labeling substance, a fluorescent pigment selected from biotin, Cy2, GFP, YO-PRO-1, YOYO-1, Calcein, FITC, FlourX, ALEXA 488, Rhodamine 110, ABI 5-FAM, Oregon Green 500, Oregon green 488, RiboGreen, Rhodamine Green, Rhodamine 123, Magnesium Green, Calcium Green, TO-PRO-1, TOTO-1, ABI JOE, BODIPY 530/550, DiI, BODIPY TMR, BODIPY558/568, BODIPY564/570, Alexa 546, TRITC, Magnesium Orange, Phycoerythrin R & B, Rhodamine Phalloidin, Calcium Orange, Pyronin Y, Rhodamine B, ABI TAMRA, Rhodamine Red, Cy3.5, ABI ROX, Calcium Crimson, Alexa 594, Texas Red, Nile Red, YO-PRO-3, YOYO-3, R-phycocyanin, C-phycocyanin, TOPRO-3, TOTO-3, DiD DiIC(5), Thiadicarbocyainie, Cy5.5, Cy5, and Cy3 is used.

When an amplification product secured by performing PCR using the analysis single-stranded nucleic acid in the complex formed by reacting the analysis single-stranded nucleic acid with the biomolecule in the biosample as a template and the primer containing the labeling substance is reacted with the capture probe, the capture probe forms complementary binding with the single-stranded nucleic acid of the amplification product containing the labeling substance, thereby forming a double-stranded nucleic acids. Therefore, in spots composed of the capture probes, when a signal based on the labeling substance is generated, the analysis single-stranded nucleic acid may be analyzed through the signal, and the protein, which is the receptor in the complex formed by the analysis single-stranded nucleic acid, may be quantitatively analyzed. Therefore, the labeling substance may be selected within various ranges depending on analysis purpose, and preferably, Cy3 or Cy5 may be used.

The present invention provides a nucleic acid chip, wherein the capture probes prepared using base sequences of the analysis single-stranded nucleic acids and the quality control single-stranded nucleic acids are affixed onto a supporter of the nucleic acid chip, and the nucleic acid chip is used to form binding information on the biomolecules and the analysis single-stranded nucleic acids for analyzing biological significance of the biomolecules in the biosample.

Further, in a nucleic acid chip for analyzing biological significance of biomolecules in a biosample according to the present invention, capture probes synthesized using at least one base sequence selected from base sequences of the determined analysis single-stranded nucleic acid and the quality control single-stranded nucleic acid and base sequences complementary thereto, or synthesized using capture probes having base sequences forming completely complementary binding with tags directing base sequences of the biomolecule-binding single-stranded nucleic acid and the quality control single-stranded nucleic acid are affixed onto the supporter.

A nucleic acid chip on which the capture probes are regularly arranged may be prepared using various methods known in the art (M. schena; DNA microarray; a practical approach, Oxford, 1999).

In addition, the nucleic acid chip for analyzing biological significance of biomolecules in a biosample according to the present invention has a configuration in which capture probes synthesized using information on the analysis single-stranded nucleic acid and the quality control single-stranded nucleic acid are affixed onto the supporter.

As long as the nucleic acid chip according to the present invention may analyze the biological significance of an unknown biomolecule with equal or similar accuracy, in view of manufacturing cost of the nucleic acid chip and analysis efficiency, it is preferable to reduce the number of capture probes affixed onto the nucleic acid chip.

The binding information indicates signals generated by complementary binding between the target probes prepared from the analysis single-stranded nucleic acid and the capture probe. Preferably, the binding information means a profile composed of spots corresponding to the capture probes configuring the supporter, and preferably, means a fluorescence intensity as a signal generated from the labeling substance in the single-stranded nucleic acid in the target probe binding to each of the capture probes configuring respective spots. The binding information is a combination of signals of the analysis target probe and the comparison target probe of the target probe. Ultimately, the binding information indicates a distribution state of single-stranded nucleic acids binding to the biomolecules in the biosample, and a distribution state of the biomolecules binding to the single-stranded nucleic acids may be deduced therefrom.

For this reason, the method for preparing a nucleic acid chip according to the present invention may further include reducing the number of capture probes to be affixed onto the nucleic acid chip according to the present invention by analyzing a degree of contribution of each of the capture probes to analyzing biological significance of the biomolecules and selecting the capture probes on the basis of the analyzed degree of contribution in a range in which the biological significance of the biomolecules may be analyzed.

In the case of analyzing a biomolecule using the nucleic acid chip according to the present invention, related data on binding information are accumulated, and a specific single-stranded nucleic acid contributing to analyzing biological significance of the biomolecule may be naturally found therefrom, such that bio markers useful for analyzing biomolecules may be naturally found.

The present invention provides a reference substance, wherein the reference substance is composed of external molecules that are not contained in a biosample, and used for quality control of an analysis process for analyzing biological significance of biomolecules in the biosample as an analysis single-stranded nucleic acid, and for quantitative analysis of the biomolecules contained in the biosample.

The present invention provides a kit for analyzing biomolecules, wherein the analysis single-stranded nucleic acid for analyzing biological significance of the biomolecules in the biosample and the reference substance are used.

The present invention provides an apparatus for analyzing biomolecules, wherein the biomolecules are analyzed by a method for analyzing biomolecules using the analysis single-stranded nucleic acid and the reference substance, and the apparatus has a system for analyzing biomolecules, the system including a sample treating device for preparing biomolecules in the biosample, and an amplification device composed a module for preparing and amplifying a biomolecule-single-stranded nucleic acid complex and a module for analyzing the amplified product.

In order to more efficiently perform the method for analyzing biomolecules according to the present invention, in an apparatus for analyzing biomolecules using an analysis binding single-stranded nucleic acid and a reference substance, including the sample treating device for separating biomolecules in the sample containing the biomolecules and the amplification device composed of the module for preparing and amplifying the biomolecule-analysis single-stranded nucleic acid and reference-single-stranded nucleic acid complex and the module for analyzing the amplified product, the system according to the present invention may be composed of the sample treating device including a mixing chamber, a lysing chamber, and a reaction chamber, and the amplification device, and the sample treating device and the amplification device may be combined with each other to thereby be used.

Analysis of a sample suspected to contain target biomolecules is accompanied with a series of sample preparing steps, and is performed in a sample treating device composed of the mixing chamber and the lysing chamber. These steps may include filtration, cell lysis, preparation of biomolecules and a biomolecule-single-stranded nucleic acid complex, and mixing with a reagent. In order to have confidence in a biomolecule analysis result, it is useful to control contamination in a sample preparing process. A method for preparing a sample for a nucleic acid amplification reaction, and for verifying effectiveness of sample preparation may be provided.

The sample is suspected to contain a target entity selected from the group consisting of cells, spores, microorganisms, and viruses, and the target entity contains at least one target biomolecule. The method includes introducing the sample into a device having a mixing chamber for mixing the sample with a sample preparation control. The sample preparation control is selected from the group consisting of cells, spores, microorganisms, and viruses, and contains a quality control substance. The device also includes a lysing chamber and a reaction chamber. The sample is mixed with the sample preparation control with each other in the mixing chamber.

The method also includes: subjecting the sample preparation control and the target entity, if the target entity is present in the sample, to lysis treatment in the lysing chamber to purify the biomolecules; forming the biomolecule-single-stranded nucleic acid complex; exposing the biomolecule-single-stranded nucleic acid complex in the lysing chamber to nucleic acid amplification conditions in the reaction chamber; and detecting the presence or absence of at least one quality control substance. Positive detection of the quality control substance indicates that the sample preparation process was satisfactory, but it was impossible to detect the quality control substance, which means that the sample was inappropriately prepared.

The present invention provides an amplification device for preparing a sample for a nucleic acid amplification reaction and for verifying effectiveness of sample preparation. The sample is suspected to contain a target entity selected from the group consisting of cells, spores, microorganisms, and viruses, and the target entity contains at least one target biomolecule. The device includes a body having a first chamber accommodating the sample preparation control to be mixed with the sample therein. The sample preparation control is selected from the group consisting of cells, spores, microorganisms, and viruses, and contains the quality control substance.

The body also includes a lysing chamber for subjecting the target entity, if present in the sample, and the sample preparation control to lysis treatment to release biomolecules therefrom and separate the biomolecule-single-stranded nucleic acid complex. Further, the body includes a lysing chamber reacting the released biomolecule and an analysis single-stranded nucleic acid to form a biomolecule-single-stranded nucleic acid complex. The body also includes a reaction chamber for holding a nucleic acid for amplification and detection.

The device further includes at least one flow controller for guiding the sample mixed with the sample preparation control so as to flow from the first chamber into the lysing chamber and for guiding the biomolecule released in the lysing chamber so as to flow into the reaction chamber.

In some exemplary embodiments, the lysing chamber accommodates an enzyme, at least one filter, and a solid state substance therein, in order to capture the target entity, if present in the sample, and the sample preparation control when the sample flows through the lysing chamber. In addition, the device further includes at least one waste chamber for accommodating used sample fluid that has flowed through the lysing chamber, and the at least one flow controller may also guide the used sample fluid that has flowed through the lysing chamber so as to flow into the waste chamber.

In some exemplary embodiments, the device further includes an ultrasonic transducer coupled to a wall of the lysing chamber to sonicate the lysing chamber. In some exemplary embodiments, the device further includes beads in the lysing chamber for rupturing the sample preparation control and the target entity.

According to another aspect of the present invention, there is provided a method for determining effectiveness of a lysis process. This method includes mixing a sample suspected to contain a target entity selected from the group consisting of cells, spores, microorganisms, and viruses with a sample preparation control. The target entity contains at least one quality control substance. The sample preparation control is selected from the group consisting of cells, spores, microorganisms, and viruses, and contains the quality control substance. A mixture of the sample preparation control and the target mixture, if present in the sample, is subjected to lysis treatment. The method further includes detecting the presence or absence of the quality control substance so as to determine whether or not biomolecules are released from the sample preparation control during the lysis treatment. Positive detection of the quality control substance indicates that the sample preparation process was satisfactory, but it was impossible to detect the quality control substance, which means that the sample was inappropriately prepared.

In some exemplary embodiments, the method includes allowing the sample mixed with the sample preparation control to flow through the chamber accommodating the solid-phase substance therein, in order to allow the sample preparation control and the target entity, if present in the sample, to be captured by the solid phase material, prior to the lysis treatment.

In some exemplary embodiments, the sample may be pre-filtered before the sample is mixed with the sample preparation control. In some exemplary embodiments, lysis treatment includes exposing the sample preparation control and the target entity to ultrasonic energy. In some exemplary embodiments, lysis treatment also includes agitating beads for rupturing the sample preparation control and the target entity. In some exemplary embodiments, the sample preparation control is a spore. In some exemplary embodiments, the mixing includes dissolving a dried bead containing the sample preparation control.

In some exemplary embodiments, lysis treatment includes contact with a chemical lysis agent. In some exemplary embodiments, a marker nucleic acid sequence is detected by amplifying the marker nucleic acid (for example, by PCB) and detecting the amplified marker nucleic acid sequence. In some exemplary embodiments, the amplified marker nucleic acid sequence is detected by determining if a signal from a probe capable of binding to the marker nucleic acid sequence exceeds a threshold value.

A reaction mixture in a reaction chamber of a reaction vessel of the amplification device is exposed to nucleic acid amplification conditions. Amplification of an RNA or DNA template using reactions is well known [U.S. Pat. Nos. 4,683,195 and 4,683,202; PCR Protocols: A Guide to Methods and Applications (Innis et al., eds, 1990)]. Amplification of DNA involves repeated cycles of heat-denaturing the DNA, annealing two oligonucleotide primers to sequences flanking the DNA segment to be amplified, and extending the annealed primers with DNA polymerase. The primers hybridize to opposite strands of a target sequence and are oriented so that DNA synthesis by the polymerase proceeds across the region between the primers, thereby effectively doubling the amount of the DNA segment. Moreover, because the extension products are also complementary to and capable of binding to primers, each successive cycle essentially doubles the amount of DNA synthesized in the previous cycle. This results in the exponential accumulation of the specific target fragment, at a rate of approximately $2^n$ (here, n is the number of cycles). Methods such as the amplification reaction and ligase chain reaction (LCR) may be used to directly amplify nucleic acid sequences. Isothermic amplification reactions are also known and may be used according to the methods of the invention.

The nucleic acid amplification reaction is preferably carried out using a thermal processing instrument that heats and/or cools the reaction mixture in the reaction vessel to the temperatures needed for the amplification reaction. The thermal processing instrument as described may also include one or more detection mechanisms for detecting a marker nucleic acid sequence of the sample preparation control and one or more target nucleic acid sequences for which the sample is being tested. A preferable thermal processing instrument embedded with optical detectors for amplifying and detecting nucleic acid sequences in the reaction vessel (U.S. Pat. Nos. 6,369,893 and 6,391,541,) may be used. In addition, there are also many other known methods for controlling a temperature of a reaction mixture and detecting nucleic acid sequences in the reaction mixture that are suitable for the present invention.

Further, it is preferable that detection of the quality control substance of the sample preparation control and detection of one or more quality control substances for which the sample is being tested is carried out using probes. It is preferable that the reaction vessel has one or more transparent or light-transmissive walls through which signals from the probe may be optically detected. Preferably, capture probes may be used to detect and quantify the nucleic acid sequences. There are many different types of assays that employ nucleic acid capture probes. Some of these capture probes generate signals with a change in the fluorescence of a fluorophore due to a change in its interaction with another molecule or moiety.

As another method for detecting amplification products, a fluorogenic probe consists of an oligonucleotide labeled with a fluorescent reporter dye module. Cleavage of the capture probe generates an increase in the fluorescence intensity of the reporter dye.

In order to confirm detection of a target biomolecule in a sample or absence thereof, there is a need to remove contamination of sample preparation. This is the reason why a sample preparation control should be subjected to the same treatment as a target entity (for example, a target cell, a spore, a virus, or a microorganism, containing biomolecules) in a sample. When the quality control substance of the sample preparation control is detected, sample preparation is considered to be satisfactory. When it is impossible to detect the presence of the quality control substance, sample preparation is considered to be inappropriate, and a test result for a target nucleic acid sequence is considered to be "undetermined". Preferably, the presence or absence of the quality control substance is detected by determining whether or not a signal from the capture probe capable of binding to the target probe exceeds a limit value, for example, a predetermined fluorescence limit value that needs to be satisfied or exceed in order to consider an analysis method to be effective.

A fluid control device may be controlled by a computer according to a desired protocol. In the case of using a single value, since a failure factor is only one, a high preparation yield may be obtained. A compact device (for example, a small cartridge form) may be obtained by integration of fluid control and treatment constitution members, which may facilitate automation of molding and assembly. As described above, it may be advantageous that this system has dilution and mixing capability, intermediate wash capability, and positive pressurization capability. A fluid path in the system is generally closed, in order to minimize contamination of the fluid in the system and to facilitate accommodation and control of the fluid. The reaction vessel is conveniently detachable and replaceable, and may be disposable in some embodiments.

The present invention provides a method and an apparatus for analyzing biomolecules, wherein a configuration for analyzing biological significance using data on binding information on the biomolecules and analysis single-stranded nucleic acids includes: a module for receiving data on binding information between the biomolecules and the analysis single-stranded nucleic acids in a patient group and binding information between the biomolecules and the analysis single-stranded nucleic acids in a control group to construct databases; a module for performing pre-processing in an analysis system using the received data on binding information; a module for generating a patient model using the pre-processed result; a module for loading the generated model and applying the loaded model to a visiting patient to perform diagnosis corresponding to a blind test; and a module for evaluating performance of the system through cross validation.

In the present invention, a system for predicting biological significance using data on binding information on the biomolecules and the analysis single-stranded nucleic acids may be used, for example, in diagnosis, but is not limited thereto.

The data on binding information on various biomolecules and analysis single-stranded nucleic acids, generated according to the present invention, may generate various information associated with cells, tissue, or diseases, which are a huge amount of information having high-level characteristics. In the module for performing pre-processing in the analysis system using the received data, a multivariate analysis method for searching features affecting a state of a patient and improving classification performance is a feature selection method for searching important variables for accurate diagnosis and treatment to search main features through dimensional reduction or characteristics modification.

As the feature selection method, there is an unsupervised learning method or a supervised learning method depending on whether or not class information is used in learning. In principal component analysis (PCA) or independent component analysis (ICA) mainly used in the unsupervised learning method, features may be extracted in consideration of characteristics of variables. The supervised learning method is a method for selecting a variable by utilizing statistical significance between class information and variables or correlations between the variables. In this method, main features may be extracted through performance applied to a classifier while sequentially adding features to a given feature set or removing the features from the given feature set in a forward or backward direction.

A module for performing learning to generate a patient model using the pre-processed result performs a procedure of classifying the selected features depending on class through a suitable classifier.

In the present invention, an artificial neural network is used, and since behaviors are determined depending on input and output, the artificial neural network has been applied in various fields such as pattern recognition, function approximation, classification methods, and the like. A structure of the artificial neural network is composed of a plurality of layers, nodes, and neural connection weights. A neural inter-connection method used in the present invention is a feed-forward method. An output value is calculated using the neural connection weight and an activation function for each node depending on an input pattern. When specific work is processed using the generated binding information, in the case in which an estimated value and an actual value are different from each other, a method of repeating a process of reducing an error while comparing a calculated value with an actual result value is the feed-forward method.

The present invention provides a method and an apparatus for analyzing biomolecules, wherein a method for selecting the patient model is selected from the group consisting of linear model methods, support vector machine methods, neural network methods, classification and regression tree methods, ensemble learning methods, discriminant analysis methods, a nearest neighbor method, Bayesian network methods, and independent components analysis methods.

In most of the diseases of which accurate and comprehensive mechanisms are not found, diagnosis based on cases is significantly important. However, in an existing case based a machine learning and reasoning system designed only based on a specific machine learning technique, accuracy is low, such that the development for an improved system is continuously required. Further, the existing system is designed only as a discriminator of disease, using all learned clinical test items, and a method for utilizing importance or the order of priority of the clinical test items depending on the kind of disease is not provided.

The present invention, which relates to a system for diagnosing a disease and selecting test items using a case based a machine learning and reasoning technology for supporting accurate disease diagnosis by a doctor, relates to a system for analyzing test information of a novel patient using a discriminator of disease to identify a disease, and providing the minimum test items required for finally identifying each disease by preliminary diagnosis, wherein the discriminator is a machine learner using a artificial neural network trained through case databases on patients. In the method for diagnosing a disease through machine learning and reasoning, the machine learning technique is individually applied. As a method for selecting the patient model, there are linear model methods, support vector machine methods, neural network methods, classification and regression tree methods, ensemble learning methods, discriminant analysis methods, a nearest neighbor method, Bayesian network methods, independent components analysis methods, and the like.

In view of configuration and actual application, the present system may be divided into two systems. That is, the present system may be divided into a stand-alone diagnosis system only for diagnosis and an integration system linked with existing hospital information systems, that is, an order communication system (OCS), a picture archiving and communication system (PACS), a laboratory information system (LIS), and the like. For cooperation with the integration system, a system needs to be configured based on HL& and DICOM standards. The present system is in cooperation with a patient monitoring system (PMS) as an early model, thereby increasing accuracy of diagnosis. In addition, the present system may be developed as a system in cooperation with various medical information systems such as OCS, electronic medical record (EMR), PACS, and the like, as well as PMS, thereby making it possible to develop a more accurate diagnosis system including various disease factors.

The present invention provides a method for analyzing biomolecules using analysis single-stranded nucleic acids and a reference substance, wherein a biosample is selected from the group consisting of bacteria, fungi, viruses, cell lines, and tissue, and the biomolecule is at least one selected from the group consisting of proteins, carbohydrates, lipids, polysaccharides, glycoproteins, hormones, receptors, antigens, antibodies, and enzymes.

MODE FOR INVENTION

Hereinafter, a method for preparing a reference substance and a biochip according to the present invention, and a method for analyzing biomolecules in a biosample composed of two or more biomolecules using the same will be described in detail with reference to accompanying drawings and Examples. The following Examples are provided for illustrative purposes, but should not be construed as limiting the scope of the present invention.

EXAMPLE 1

Preparation of Single-stranded Nucleic Acid Having Random Base Sequence

Polymerase chain reaction (PCR) was performed using single-stranded DNA oligonucleotides having the following random base sequence to prepare double-stranded DNAs, followed by in vitro transcription of the double-stranded DNAs, thereby preparing a single-stranded RNA library (random single-stranded nucleic acids).

5'-GGGAGAGCGGAAGCGTGCTGGGCC N40
CATAACCCAGAGGTCGATGGATCCCCCC-3'

(Here, underlined base sequences are invariable regions and N40 means sequence sites at which bases such as adenine (A), guanine (G), thymine (T), cytosine (C), and the like, are randomly present at respective positions.

5'-GGGAGAGCGGAAGCGTGCTGGGCC-3'
and

5'-CATAACCCAGAGGTCGATGGATCCCCCC-3' are identified as SEQ ID NO. 1 and 2 respectively.)

A forward (FW) primer used in PCR may form base pairing with 5'-terminals of the underlined bases of the above base sequence, and include a promoter base sequence for RNA polymerase of bacteriophage T7.

A reverse (RE) primer used in the PCR may form base pairing with 3'-terminals of the underlined bases of the above base sequence. In addition, the FW and RE primers may contain base sequences (restriction enzyme cleavage sites) for EcoRI, BamHI, and the like, respectively, for subsequent cloning.

Random single-stranded nucleic acids to be reacted with a biosample constitute an RNA library containing 2'-F-substituted pyrimidines. In addition, DNA library transcripts and PCR primers were designed as described above and prepared by PCR and in vitro transcription.

PCR was performed with 1,000 pmoles of single-stranded DNA serving as a template, in the presence of 2,500 pmoles of a pair of PCR primers (5P7) in a buffer solution containing 50 mM KCl, 10 mM Tris-Cl (pH 8.3), 3 mM $MgCl_2$, 0.5 mM dNTP (dATP, dCTP, dGTP, and dTTP), and 0.1 U Taq DNA Polymerase (Perkin-Elmer, Foster City Calif.), followed by purification of the PCR product through QIAquick-spin PCR columns (QIAGEN Inc., Chatsworth Calif.).

Single-stranded nucleic acids containing 2'-F-substituted pyrimidines were synthesized through in vitro transcription, and purified. 200 pmoles of double-stranded DNAs, 40 mM Tris-Cl (pH 8.0), 12 mM $MgCl_2$, 5 mM DTT, 1 mM spermidine, 0.002% Triton X-100, 4% PEG 8000, 5 U T7 RNA Polymerase, ATP and GTP (each 1 mM), and 2'F-CTP and 2'F-UTP (each 3 mM) were reacted at 37° C. for 6 to 12 hours, followed by purification through a Bio-Spin 6 chromatography column (Bio-Rad Laboratories, Hercules Calif.). Amounts and purities of the purified nucleic acids were analyzed using a UV spectrometer.

EXAMPLE 2

Preparation of Biomolecule-binding Single-stranded Nucleic Acid Binding to Human Serum Protein 2-1. Securing of Biomolecule-Single-stranded Nucleic Acid Complex 2-1-1. Washing Method In the present invention, a biosample composed of two or more biomolecules was an example of human serum proteins. A solution containing the random single-stranded nucleic acids synthesized in Example 1 at a concentration of $10^{15}$ base sequences/L was added in an amount of 200 pmol/L to a selection buffer (50 mM Tris-Cl (pH 7.4), 5 mM KCl, 100 mM NaCl, 1 mM $MgCl_2$, and 0.1% $NaN_3$), heated at 80° C. for 10 minutes, and allowed to stand on ice for 10 minutes. A reaction solution was prepared by adding yeast tRNA (Life Technologies) in an amount five times as much as the used single-stranded nucleic acids and 0.2% bovine serum albumin (BSA, Merck) thereto.

After 10 μL of a serum biosample containing an external reference substance was added to 90 μL of the reaction solution, a nitrocellulose membrane disc was soaked therein, and a reaction was performed for 30 minutes with shaking. The disk to which the serum biosample was attached was treated with the prepared RNA single-stranded nucleic acids and a reaction was performed for 30 minutes.

After reaction, unbound RNA single-stranded nucleic acids were removed by repeating a washing process with a washing buffer as described below, such that human serum protein (biomolecule)-single-stranded nucleic acid complexes to be used to prepare single-stranded nucleic acids binding to human serum proteins of the human serum biosample were secured by a single selection process.

As the washing buffer for securing the biomolecule-single-stranded nucleic acid complexes, 0 to 1×SELEX buffer or 0 to 500 mM EDTA solution was used. Further, in order to prepare single-stranded nucleic acid binding to the external reference substance, an external reference substance-single-stranded nucleic acid complex may be secured together with the human serum protein-single-stranded nucleic acid complexes.

As the external reference substance, after five plant-specific proteins were selected and proteins corresponding thereto were expressed using an E. coli expression system, the expressed proteins were separated, and a single-stranded nucleic acid binding to the external reference substance was secured by SELEX. A capture probe corresponding to the external reference substance was designed using a base sequence of the secured single-stranded nucleic acid.

2-1-2. Capillary Electrophoresis

A solution containing the synthesized random single-stranded nucleic acids at a concentration of $10^{15}$ base sequences/L was added in an amount of 200 pmol/L to a reaction solution (100 mM Tris-HCl (pH 8.2), 200 mM NaCl, and 10 mM $MgCl_2$), heated at 80° C. for 10 minutes, and allowed to stand on ice for 10 minutes. A reaction solution was prepared by adding yeast tRNA (Life Technologies) in an amount five times as much as the used single-stranded nucleic acids and 0.2% bovine serum albumin (BSA, Merck) thereto.

10 μl of a serum biosample was added to 90 μl of the reaction solution and a reaction was carried out for 30 minutes. The reaction mixture solution was subjected to capillary electrophoresis using a buffer solution (50 mM Tris-HCl, pH 8.2). All analyses using the capillary electrophoresis in the present invention were performed using a P/ACE 5000 CE-LIF system (Beckman Coulter) equipped with fused-silica capillary (Beckman Coulter; length of 37 cm, inner diameter of 75 m). A fluorescent substance was excited by a 3 mW Ar-ion laser (488 nm) attached to the system to emit signals through a 520 nm filter, and the signals were detected by a detector in the LIF system.

All solutions used in the analysis and capillary treatment were filtered through a filter having pore size of 0.2 μm. The capillary tubes were washed by flowing 1 N NaOH and distilled water for 5 minutes therein, respectively, and then used, and between runs, sequentially washed with 1 N NaOH, distilled water, and the buffer solution for 2 minutes each.

Electrophoresis was performed by applying a voltage of 10.8 kV thereto, and the results were analyzed. It was confirmed through a graph obtained by analyzing formation of the biomolecule-single-stranded nucleic acid complex using capillary electrophoresis that the biomolecule-single-stranded complex was specifically formed and separated.

RT-PCR was performed on the separated complex, thereby amplifying and preparing a DNA pool directing RNAs (biomolecule-binding single-stranded nucleic acids) binding to the serum proteins. Here, the selection and amplification process may be repeated several times to prepare biomolecule-binding single-stranded nucleic acids.

2-1-3. Structure of Nitrocellulose and Nylon

A solution containing the synthesized random single-stranded nucleic acids at a concentration of $10^{15}$ base sequences/L was added in an amount of 200 pmol/L to a reaction solution (100 mM Tris-HCl (pH 8.2), 200 mM NaCl, and 10 mM $MgCl_2$), heated at 80° C. for 10 minutes, and allowed to stand on ice for 10 minutes. A reaction solution was prepared by adding yeast tRNA (Life Technologies) in an amount five times as much as the used single-stranded nucleic acids and 0.2% bovine serum albumin (BSA, Merck) thereto.

10 μl of a serum biosample was added to 90 μl of the reaction solution and the prepared RNA single-stranded nucleic acids were reacted for 30 minutes, thereby forming biomolecule-single-stranded nucleic acid complexes.

In order to select biomolecule-binding single-stranded nucleic acids binding to a human serum biosample (biomolecules), when the reaction mixture solution was treated with a structure made of nitrocellulose and nylon and a pressure was applied thereto, the single-stranded nucleic acid complexes were present on a nitrocellulose filter, and unbound single-stranded nucleic acids were present on a nylon membrane. The human serum protein (biomolecule)-single-stranded nucleic acid complexes were secured through a single selection process by collecting the nitrocellulose filter and repeating a washing process with various washing buffers to remove the unbound single-stranded nucleic acids present on the nitrocellulose filter.

As the washing buffer for securing the biomolecule-single-stranded nucleic acid complexes, 0 to 1×SELEX buffer or 0 to 500 mM EDTA solution was used.

2-2. Preparation of Biomolecule-Binding Single-stranded Nucleic Acids

RT-PCR was performed on the secured complexes, thereby amplifying and preparing a pool of DNAs directing RNAs (biomolecule-binding single-stranded nucleic acids) binding to the serum proteins. Here, the selection and amplification process may be repeated several times to prepare biomolecule-binding single-stranded nucleic acids.

The secured RT-PCR product, DNA, was cloned into plasmids to secure individual clones, thereby completing preparation of the biomolecule binding-single-stranded nucleic acids. The plasmids were separated and used to determine base sequences of the biomolecule-binding single-stranded nucleic acids.

Base sequences of capture probes to be used in a nucleic acid chip for generating profiles of biomolecules according to the present invention were designed using information on base sequences of the single-stranded nucleic acids binding to the human serum proteins (biomolecules). Thus, in order to select the single-stranded nucleic acids and prepare the capture probes, after confirming secondary structures and the free energies of the secondary structures using a MFOLD program for modeling the secondary structures of nucleic acids, single-stranded nucleic acids having the most stable secondary structures were selected, and the capture probes were designed on the basis of the selected single-stranded nucleic acids.

EXAMPLE 3

Preparation of Quality Control Single-stranded Nucleic Acid

A reference substance was composed of five kinds of plant specific proteins A, B, C, D, and E secured from the plant specific database (genomics.msu.edu/plant_specific/) (see Table 1).

TABLE 1

Plant Specific Proteins

| Kind | Locus) | Content | Accession number |
|---|---|---|---|
| A | At1g65390.1 | defense/immunity protein | GO: 0003793 |
| B | At5g39310.1 | cell elongation | GO: 0009826 |
| C | At4g15910.1 | Drought-Induced Protein (Di21) | GO: 0009414 |
| D | At1g12860.1 | Bhlh Protein | GO: 0003677 |
| E | At4g02530.1 | Chloroplast Thylakoid Lumen Protein | GO: 0009543 |

After expressing proteins corresponding to the selected five plant specific proteins using an *E. coli* expression system, the expressed proteins were separated and single-stranded nucleic acids binding to the reference substance were secured by a standard SELEX method (Ellington, A. D. and J. W. Szostak. 1990. In vitro selection of RNA molecules that bind specific ligands. Nature 346: 818-822; Gold, L., P. Allen, J. Binkley, D. Brown, D. Schneider, S. R. Eddy, C. Tuerk, L. Green, S. Macdougal, and D. Tasset. 1993. RNA: the shape of things to come, pp. 497-510. In: R. F. Gestelend and J. F. Atkins (eds.). The RNA World, Cold Spring Harbor Press, Cold Spring Harbor, N.Y.). The obtained single-stranded nucleic acids were referred to as quality control single-stranded nucleic acids, and capture probes corresponding to the quality control single-stranded nucleic acids were designed using base sequences of the quality control single-stranded nucleic acids.

EXAMPLE 4

Preparation of Biochip (Nucleic Acid Chip)

As capture probes to be affixed onto a surface of a glass slide, single-stranded nucleic acids (oligonucleotides) having base sequences complementary to those of the approximately 3,000 biomolecules binding single-stranded nucleic acids selected in Example 1 and the quality control single-stranded nucleic acids were organically synthesized (Bioneer, Korea), thereby preparing the capture probes.

A nucleic acid chip was prepared on which the capture probes were arranged in a constant order using an Ultra-GAPS™ Coated Slide (Corning Inc.), a gamma amino propyl silane (GAPS)-coated glass slide. The nucleic acid chip was manufactured using a microarrayer system (Gen-Pak) operating in a pin type while the spot spacing of the arrays was set to be 370 μm center-to-center. Each of the capture probes were dissolved in a standard solution, thereby adjusting a concentration thereof. In this case, a humidity of 70% was maintained inside the arrayer system while it performed spotting. After being kept in a humidified chamber for 24 to 48 hours, the spotted slides were baked in a UV crosslinker. After the capture probes were fixed to the glass slides using a widely known method, the slides were dried by centrifugation and stored in a light-tight place.

EXAMPLE 5

Preparation of Target Probe

The same amounts of plasmids in which the single-stranded nucleic acids prepared in Example 2 and used to prepare the biochip (nucleic acid chip) were inserted, and plasmids into which the quality control single-stranded nucleic acids prepared in Example 3 were inserted were mixed with each other, thereby preparing a plasmid pool. In addition, a pool of the single-stranded nucleic acids binding to human serum proteins, or the like, was prepared as described below through PCR and in vitro transcription after designing and preparing the plasmid pool and PCR primers.

PCR was performed for 30 cycles of 30 seconds at 94° C., 30 seconds at 52° C., and 20 seconds at 72° C. in a PCR reaction solution containing 100 pM 5'-primers, 100 μM 3'-primers and a dNTP mixture (5 mM DATP, 5 mM CTP, 5 mM dGTP, and 5 mM dTTP) using 1 pg of the plasmid pool as a transcript by a standard PCR method to synthesize double-stranded nucleic acids, followed by purification through a QIAquick-spin PCR column (QIAGEN Inc., Chatsworth Calif.).

Single-stranded nucleic acids of RNA molecules containing 2'-F-substituted pyrimidines were synthesized through in vitro transcription, and purified.

200 pmoles double-stranded DNAs, 40 mM Tris-Cl (pH 8.0), 12 mM $MgCl_2$, 5 mM DTT, 1 mM spermidine, 0.002% Triton X-100, 4% PEG 8000, 5 U T7 RNA Polymerase, ATP and GTP (each 1 mM), and 2'F-CTP and 2'F-UTP (each 3 mM) were reacted at 37° C. for 6 to 12 hours, followed by purification through a Bio-Spin 6 chromatography column (Bio-Rad Laboratories, Hercules Calif.).

A reference substance I in which different amounts of the reference substances were contained was added to a phosphate buffered saline (PBS) solution. The reference substance I was composed of five kinds of plant specific proteins, biomolecules A, B, C, D, and E (see Table 1). The reference substance I was composed of the external biomolecule A (0.01 pg/ml), the external biomolecule B (1.0 pg/ml), the external biomolecule C (100.0 pg/ml), the external biomolecule D (10.0 ng/ml), and the external molecule E (1.0 μg/ml).

The human serums used in analysis were serums taken from a healthy person and a cardiovascular disease patient, stable angina pectoris patient, and a biosample was prepared by adding 10 μl of serum biosample to 90 μl of the PBS solution to which the reference substance I was added, and putting a nitrocellulose membrane disc thereinto to perform a reaction for 30 minutes while shaking. 100 to 400 ng of the single-stranded nucleic acids prepared above were added thereto, and reactions were performed for 30 minutes, thereby forming biomolecule-single-stranded nucleic acid complexes.

The resultant was washed with a selection buffer or 50 mM EDTA three times, and the disc to which protein-single-stranded nucleic acids were attached was separated and collected.

After the collected disc to which the protein (biomolecule)-single-stranded nucleic acids were attached, or a disc to which the external reference substance as an analysis target probe and the protein (biomolecule)-single-stranded nucleic acids were attached was added to a RT-PCR solution to perform reverse transcription, an amplification reaction was performed thereon using a Cy-5 labeled primer (5'-Cy5-CGGAAGCGTGCTGGGCC-3', SEQ ID NO. 3), thereby preparing an analysis target probe, a Cy-5 labeled single-stranded nucleic acid. Reverse transcription was performed by the same method as described above using the single-stranded nucleic acids prepared from the plasmid pool obtained by mixing the same amounts of the plasmids for the serum proteins and the plasmids for the external reference substance with each other, and an amplification reaction was performed using a Cy-3 labeled primer (5'-Cy3-CG-GAAGCGTGCTGG GCC-3', SEQ ID NO. 4), thereby preparing a comparison target probe, a Cy-3 labeled single-stranded nucleic acid. The two solutions were mixed with each other in the same amounts, thereby preparing a target probe containing the analysis target probe and the comparison target probe.

EXAMPLE 6

Hybridization Reaction of Biochip (Nucleic Acid Chip) and Target Probe Solution The target probe solution prepared in Example 4 was treated with the capture probe of the biochip (nucleic acid chip) of the present invention to thereby be hybridized at 60° C. for 4 to 12 hours, and then washed with 0.1×SSC solution at 42° C. Here, a hybridization solution contained 1 M sodium chloride, 0.3 M sodium citrate, 0.5% SDS or 100/ml salmon sperm DNA, and 0.2% bovine serum albumin or single-stranded nucleic acids.

After completion of pre-hybridization, the glass slide was treated with the target probe solution prepared in Example 3 to conduct hybridization at 42° C. for 12 hours, followed by washing the nucleic acid chip with washing solutions. Here, compositions of the washing solutions were sequentially 1×SSC+0.2% SDS, 1×SSC+0.2% SDS, 0.5×SSC+0.2% SDS, and 0.01×SSC+0.2% SDS, and the washing was performed at 42° C. for 30 minutes for each solution.

EXAMPLE 7

Search and Analysis of Spots on Biochip (Nucleic Acid Chip)

After completion of the washing in Example 6, the glass slide was dried by centrifugation and scanned with a laser scanner (GenePix4000, Axon Corp.) using laser light of a wavelength (635 nm) suitable for exciting a fluorescent dye (Cy5). Fluorescent images were captured as multi-image-tagged image file format and analyzed with a suitable image analysis software (GenePix Pro 3.0, Axon).

Signal intensity per spot (unit: quanta) from which basic signals of a neighboring background (that is, background signals) were subtracted was used. Here, the term "background signals" means signals of a local background consisting of four spots neighboring a specific spot. Generally, when 90% or more pixels of the spot have a signal intensity over background signal+2 standard deviations (S. D.), the spot is used for data analysis; otherwise, the spot is classified as a bad spot and is not used for data analysis.

Signal intensity was normalized against variations according to labeling efficiency using internal standard (IS) signals (e.g., Normalized Intensity=Probe Intensity/IS intensity). In the case of monolabeling, the signal intensity of Cy5 channels was recorded, and in the case in which spotting is conducted two times or more, mean values were used. For the signal intensity (S) of target single-stranded nucleic acid, signal intensity of each of the spot pixels was measured and a median value thereof (median value of pixel-by-pixel) was used. The signal intensity (S) was normalized against variations according to labeling efficiency using internal standard (IS) signals.

$$S'(\text{normalized value}) = S(\text{Cy5-reference}) \times (\text{Cy5-IS}).$$

Relationships between analysis results of pixel density and actual sample amounts were found by the method as described above, thereby making it possible to confirm the correlation therebetween. It is possible to provide a method for converting the fluorescent data of the nucleic acid chip into image and confirming a profile of biomolecules in a biosample in all spot patterns. The spot patterns may be analyzed by a method such as a hierarchical clustering method, an artificial neural network method, and the like, and then used. Fluorescent intensities of spots may vary depending on properties of double strands formed between the capture probes and the target probes The fluorescent intensity of the spot may be determined depending on amounts of the analysis target probe and the comparison target probe configuring the spot.

Figure 6:
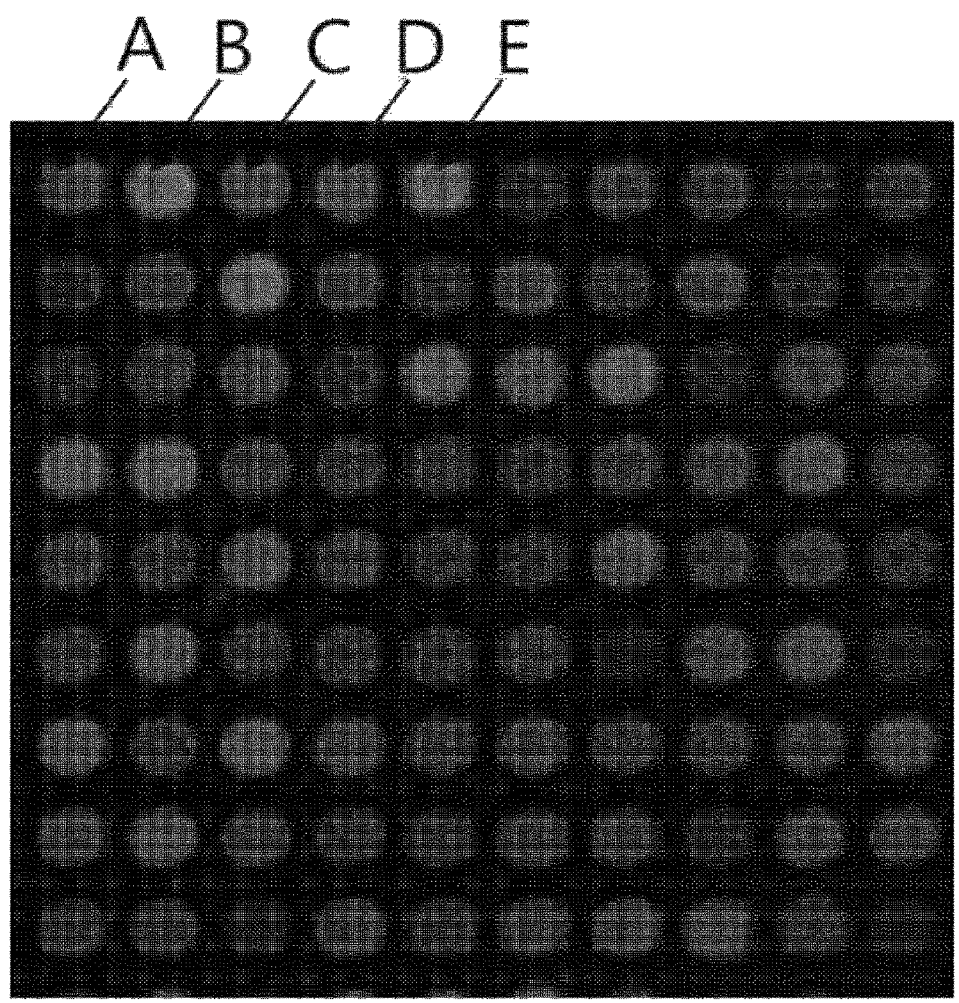
FIG. 6 is a view showing a spot corresponding to a quality control single-stranded nucleic acid corresponding to a reference substance.

First, fluorescent images according to Example 7 were shown in FIG. 6, and the reference substance was composed of five kinds of plant specific proteins, that is, the external biomolecules A, B, C, D, and E. The external biomolecule A (0.01 pg/ml), the external biomolecule B (1.0 pg/ml), the external biomolecule C (100.0 pg/m), the external biomolecule D (10.0 ng/ml), and the external molecule E (1.0 µg/ml) were added to the serum sample and analyzed. Fluorescent intensity of a spot corresponding to the reference substance will be determined by amounts of a quality control comparison target probe and a quality control analysis target probe. Since the amount of the quality control comparison target probe is known, the fluorescent intensity of the spot corresponding to the reference substance will be determined by the amount of the quality control analysis target probe to be formed from the reference substance in an analysis biosample. That is, the fluorescent intensity of the spot corresponding to the reference substance is associated with the amount of the reference substance contained in the analysis biosample. Therefore, a desired spot may be quantitatively analyzed using a fluorescent intensity of the desired spot by constructing a standard curve of correlation therebetween.

In the present experiment, since the amount of the analysis target probe was constant, the fluorescent intensity of the spot indicated the amount of the analysis target probe, and the amount of the analysis target probe indicated an amount of the human serum protein-single-stranded nucleic acid complex. Further, the amount of the complex indicated an amount of the biomolecules in the biosample. Therefore, it was possible to confirm an amount of a specific biomolecule in the biosample containing the biomolecules corresponding to the spots from the fluorescent intensities of the spots. As a result, a profile of the serum proteins in the human serum may be confirmed by analyzing fluorescent intensities of the formed spots and confirming all spot patterns of the nucleic acid chip.

That is, spectra of blue-yellow-red colors were shown in the formed spots, which was a phenomenon resulting from various ratios between the Cy-3 labeled competitive inhibitor and the cy-5 labeled target probe, both bound to the capture probes. Because the color intensity detected at a specific spot represents an amount of a specific biomolecule (protein) present in the human serum biosample, configuring the human serum, the image data formed from the color spectra of all spots on the nucleic chip correspond to profiles of biomolecules in a specific biosample.

In more detail, in the method for analyzing biomolecule according to the present invention, a target probe binding to a capture probe to form a double strand at a specific spot is composed of a Cy-3 labeled comparison target probe and a Cy-5 labeled analysis target probe, wherein the former is present in a constant amount, but the latter is present in an amount proportional to that of a biomolecule corresponding thereto in a human serum. Accordingly, a specific spot appears blue when the Cy-5 analysis target probe is present in a relatively small amount, yellow when the Cy-3 comparison target probe and the Cy-5 analysis target probe are present in similar amounts, and red when the Cy-5 analysis target probe is present in a relatively large amount.

The fluorescent intensity of spots on the nucleic acid chip varies depending on the number of analysis target probes within the double strands, which is correlated with the number of biomolecules. Therefore, the image data reflecting the color spectra of all spots configuring the nucleic acid chip of the present invention may provide profiles for the biomolecules of the biosample including unknown biomolecules.

The test results as described above are shown in FIG. 6. As shown in FIG. 6, in the glass slide to which the capture probes were attached, color spectra of blue-yellow-red colors were shown at various fluorescent intensities at spots onto which the capture probes, based on the single-stranded nucleic acids binding to serum proteins, were affixed.

EXAMPLE 8

Preparation of Solution Array Using Beads and Generation of Profile

Beads were made of one selected from the group consisting of polystyrene, polymethyl methacrylate, latex, silica, polyvinyltoluene, a styrenevinyltoluene polymer, and a styrene-butadiene polymer. In addition, a size of the micro-beads was not limited, and both a bead having an unmodified surface and a bead having a surface modified with a carboxylic group may be used.

For fixation, the surface of the micro-bead was modified with the carboxylic group, and the capture probe was fixed using an N-hydroxy succinimide (NHS)/1-ethyl-3-(3-dimethylaminopropyl)-carbodiimide (EDC) reaction.

As capture probes to be affixed onto surfaces of the beads, single-stranded nucleic acids (oligonucleotides) having base sequences complementary to those of the approximately 3,000 biomolecules binding single-stranded nucleic acids selected in Example 1 and the quality control single-stranded nucleic acid were organically synthesized (Bioneer, Korea), thereby preparing the capture probes.

8-1. Manufacturing of Bead Array

A bead array was manufactured by affixing the capture probes onto respective prepared beads (xMAP carboxylated microspheres; Luminex Corp. Austin, Tex.) using the capture probes.

Each of the capture probes was prepared at a concentration of 100 µM by dissolving the capture probes prepared in Example 4 in distilled water. After beads to be reacted were well mixed in numerical order, each 40 µl was pelleted to a freshly prepared tube (beads denoted by different numbers were prepared depending on respective probes and well-mixed, and for reactions with the probes, each 40 µl was pelleted and injected into a new tube in a state in which the beads were well-mixed.). 20 µl of 0.1 M MES buffer (pH 4.5) was mixed therewith, and 2 µl of the prepared probe was mixed with the beads. Thereafter, 1 µl of freshly prepared 10 mg/ml 1-ethyl-3-(3-dimethylaminopropyl)-carbodiimide (EDC) hydrochloride (HCl) solution (Pierce) was added thereto, and a reaction was carried out. The reaction was carried out by appropriately shaking the mixture for about 30 minutes in the dark. Again, 1 µl of freshly prepared 10 mg/ml EDC solution was additionally added thereto, followed by further reacting for about 20 minutes. Then, 500 µl of 0.020% Tween-20 solution was added to each tube and well-mixed. The bead in each tube was centrifuged to remove a supernatant from the tube, and 500 µl of 0.1% sodium dodecyl sulfate (SDS) solution was added to the tube again, followed by agitating well. The bead in each tube was centrifuged again as described above to remove a supernatant from the tube. Next, the resultant bead was dissolved in 150 µl of TE buffer (pH 8.0) and stored at 4° C. in the dark.

8-2. Formation of Profile

An analysis target probe was prepared by the same manner as in Example 5 except that the analysis target probe was a biotin labeled single-stranded nucleic acid prepared by performing an amplification reaction using a biotin labeled primer (5'-biotin-CGGAAGCGTGCTGGGCC-3').

The prepared analysis target probe was dissolved in the hybridization solution and hybridized with the hybrid bead prepared in Example 8-1. After the reaction was carried out at 95° C. for 5 minutes and at 40° C. for 30 minutes. Thereafter, after the reaction was terminated, the reactant was transferred to a 96-well filter plate, and washed with the washing buffer three times. After washing, the resultant was agitated in 100 µl of 500-fold diluted solution of streptavidin-phycoerythrin (SigmaAldirich, S3402) for 15 minutes in the dark.

The bead for each well was read in a Luminex 100 instrument using the hybrid bead sample prepared as described above. The Luminex 100 instrument used two lasers: one indicated a bead number, and the other calculated an amount of reacted phycoerythrin to indicate the calculated amount as a numerical value. An amount of the target probe binding to each of the capture probe may be determined as a mean fluorescence index (MFI) value while scanning the corresponding bead.

EXAMPLE 9

Analysis of Serum Proteins of Cardiovascular Disease Patient

It was possible to confirm a profile of serum proteins in the human serum using the nucleic acid chip based on the target single-stranded nucleic acids binding to the human serum proteins from the results of FIG. 6, and it may be confirmed that profiles of biomolecules in serums of a healthy person A and a cardiovascular disease patient (B) with stable angina pectoris were different from each other.

Figure 7:
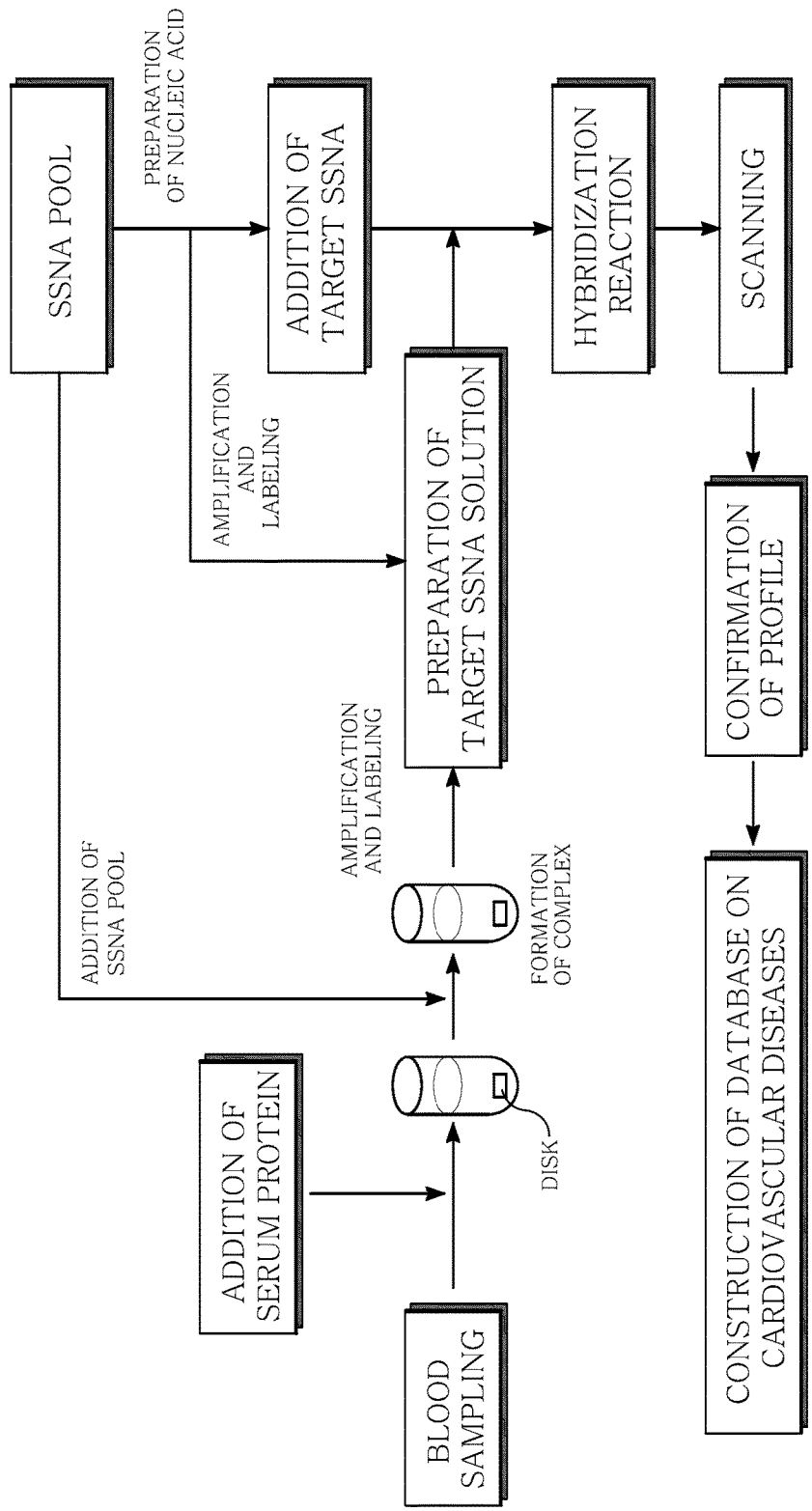
FIG. 7 is a view showing a process of diagnosing a disease using a program using a database of a human serum protein profile generated using a nucleic acid chip according to the present invention, and an artificial neural network algorithm.
Figure 8:
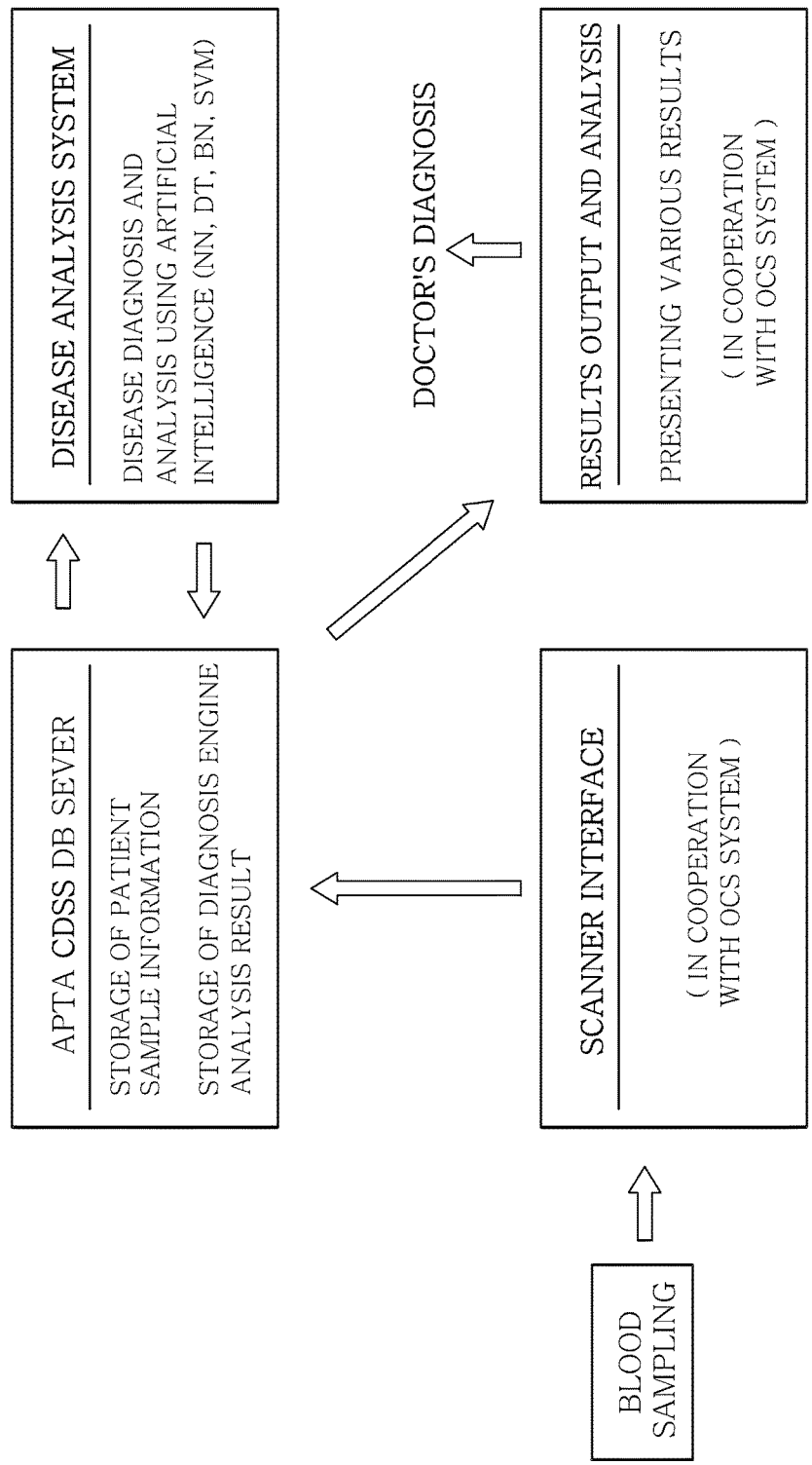
FIG. 8 is a view showing a result of diagnosing a cardiovascular disease using a program using a database of a human serum protein profile generated using a reference substance and a nucleic acid chip according to the present invention, and the artificial neural network algorithm.
Figure 9:
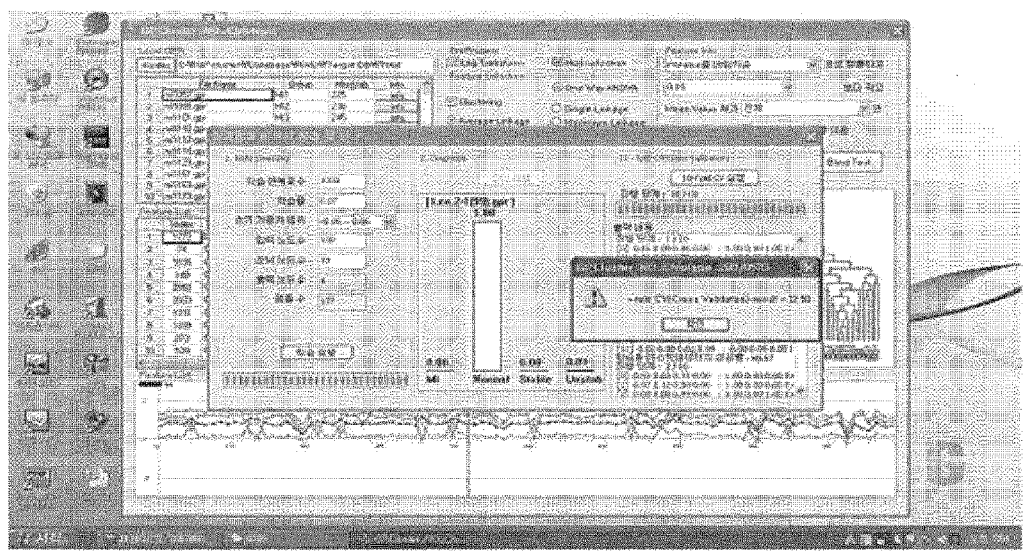
FIG. 9 is a view showing a result of diagnosing liver cancer using the program using a database of a human serum protein profile generated using the reference substance and the nucleic acid chip according to the present invention, and the artificial neural network algorithm.

FIG. 7 is a flow chart showing a sequence of a process of constructing a database of the profiles obtained from blood biosamples of patients using the nucleic chip of the present invention according to disease type. FIG. 8 is a flow chart showing a process of generating a profile of biomolecules for a serum of a specific person to diagnose a disease using database constructed from the generated profiles according to disease type and a program using an artificial neural network.

As shown in FIG. 8, database constructed with the profiled generated from various biosamples may be analyzed using bioinformatics technologies, thereby making it possible to secure useful information.

Clinical data of the serum biosamples used to construct databases for diagnosing cardiovascular diseases are summarized in the following Table 2, and the samples were obtained from a total of 127 persons including 37 healthy persons, 36 stable angina pectoris patients, 28 unstable angina pectoris patients, and 27 myocardial infarction patients. A serum sample from the person named Lee 2-1 (99) was assayed using the serum profile databases of healthy persons and patients with cardiovascular diseases including stable angina pectoris, unstable angina pectoris, and myocardial infarction, and the results are shown in FIG.

9. The subject may be predicted to be healthy with 10-fold cross validation accuracy of 72.5%.

TABLE 2

Clinical Information of Cardiovascular Disease Patients

| | Healthy Person | Stable Angina Pectoris | Unstable Angina Pectoris | Myocardial Infarction |
|---|---|---|---|---|
| Gender | | | | |
| Male | 35 | 35 | 27 | 27 |
| Female | 2 | 1 | 1 | 0 |
| Age | | | | |
| 40~49 | 1 | 0 | 1 | 0 |
| 50~59 | 13 | 17 | 15 | 17 |
| 60~69 | 22 | 18 | 11 | 10 |
| 70~79 | 1 | 1 | 1 | 0 |
| Total | 37 | 36 | 28 | 27 |

Clinical data of the serum samples used to construct databases for diagnosing liver cancer are summarized in the following Table 3, and the samples were obtained from a total of 102 persons including 19 healthy persons and 83 liver cancer patients, of which 72 were non-metastatic liver cancer patients and 11 were metastatic liver cancer patients.

After constructing a patient model of liver cancer patients and healthy persons from the database of profiles of serum proteins of liver cancer patients and healthy persons, a patient model of metastatic liver cancer patients and non-metastatic liver cancer patients was constructed from the database of the liver cancer patients.

First, whether or not a blind patient is a liver cancer patient may be determined using the patient model of the liver cancer patients and the healthy persons and a program using the artificial neural network, and continuously, a metastatic stage, a liver cancer progression stage, may be additionally confirmed in a benign liver cancer patient using the patient model of the metastatic patients and the non-metastatic patients and the program using the artificial neural network. In addition, prognosis, drug-responsibility, and the like, as well as a progression state of a disease such as the metastatic state, and the like, may also be examined.

Figure 10:
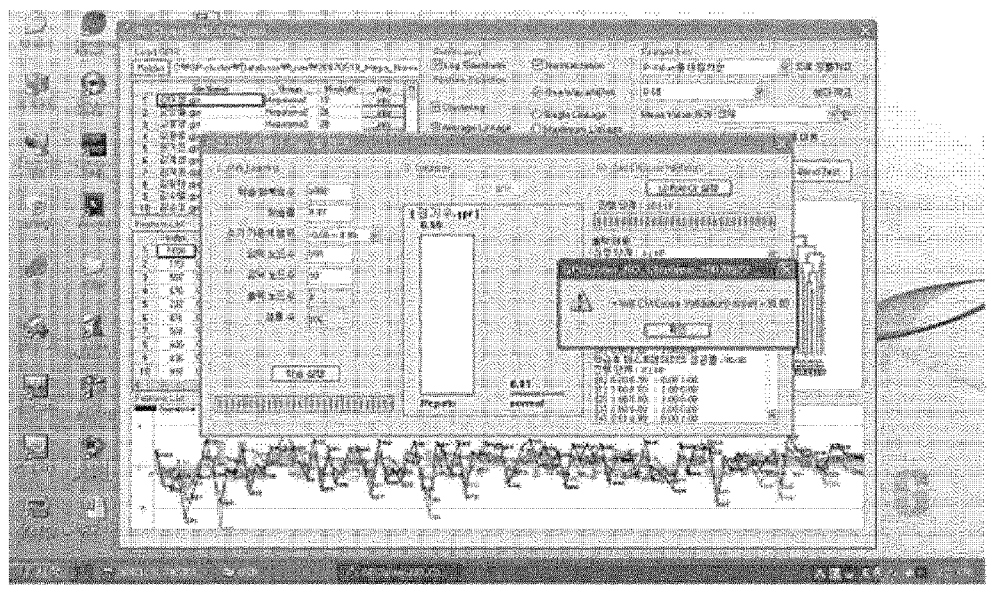
FIG. 10 is a view showing a result of diagnosing metastasis of liver cancer using the program using the database of the human serum protein profile generated using the a reference substance and the nucleic acid chip according to the present invention, and the artificial neural network algorithm.

A serum sample from the person named Kim was assayed using the serum profile databases of healthy persons and liver cancer patients, and the results are shown in FIG. 10. The subject may be predicted to be a liver cancer patient with 10-fold cross validation accuracy of 93.0%.

To determine whether or not the cancer underwent metastasis, the serum sample (of Kim) was further assayed using serum profile databases of healthy persons, and metastatic and non-metastatic liver cancer patients. As a result, the subject may be predicted to be a non-metastatic liver cancer patient with 10-fold cross validation accuracy of 76%.

TABLE 3

Clinical Information of Liver Cancer Patients

| | Healthy Person | Non-Metastatic Liver Cancer | Metastatic Liver Cancer |
|---|---|---|---|
| Gender | | | |
| Male | 17 | 67 | 11 |
| Female | 2 | 5 | 0 |
| Age | | | |
| 40~49 | 14 | 60 | 7 |
| 50~59 | 5 | 7 | 3 |
| 60~69 | 0 | 5 | 1 |
| Total | 19 | 72 | 11 |

Figure 11:
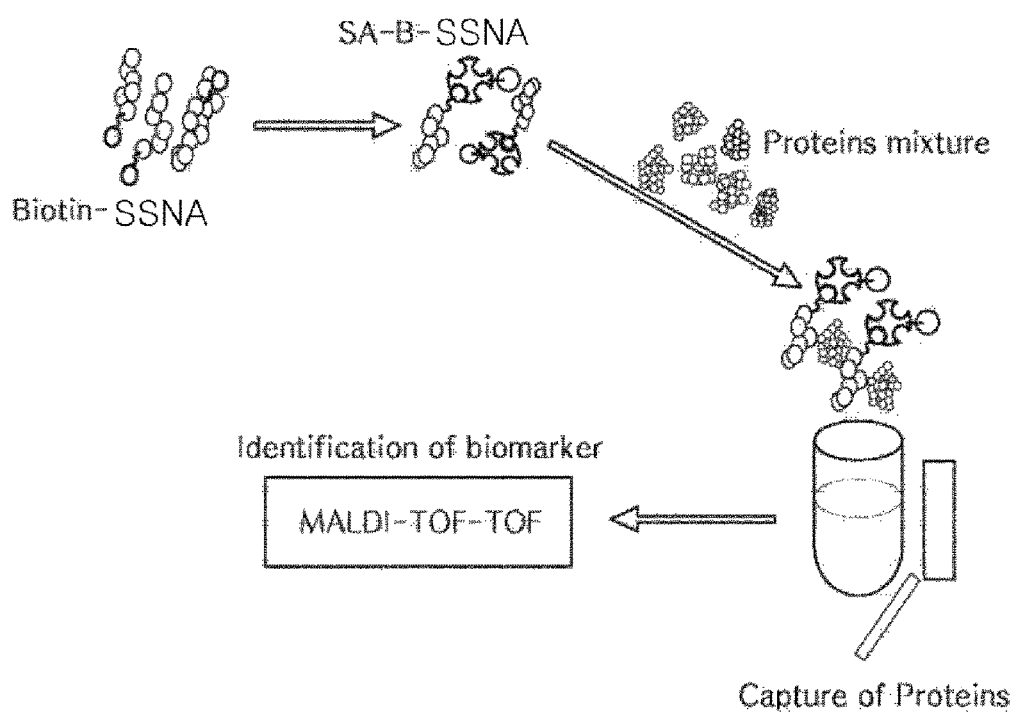
FIG. 11 is a view showing a sequence of a process of determining an amino acid sequence of a protein specifically existing in a serum of a myocardial infarction patient in the database of the human serum protein profile generated using the reference substance and the nucleic acid chip according to the present invention.
Figure 12:
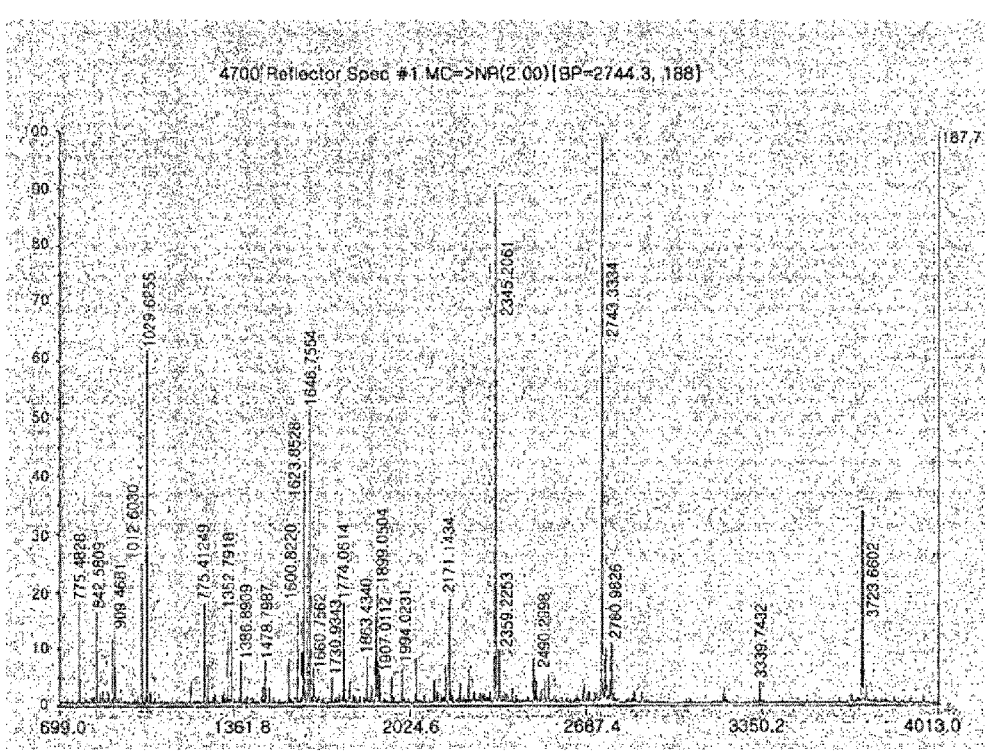
FIG. 12 is a view showing the determined amino acid sequence of the protein specifically existing in the serum of the myocardial infarction patient in the database of the human serum protein profile generated using the reference substance and the nucleic acid chip according to the present invention.

FIG. 11 is a flow chart showing a sequence of a process of comparing serum profiles between healthy persons and cardiovascular patients to determine spots peculiar to the cardiovascular disease patients, attaching biotin to single-stranded nucleic acids corresponding thereto, sequentially reacting with the single-stranded nucleic acids with streptavidin and the serum biosample, separating the resulting complexes, and separating bands formed by electrophoresis, and then identifying biomolecules. FIG. 12 is a view showing determination of an amino acid sequence of the protein bound to the selected single-stranded nucleic acid using a MALDI-TOF-TOF instrument.

Profiles of biomolecules of a specific biosample were searched and analyzed using the nucleic acid chip according to the present invention, onto which single-stranded nucleic acids based on the single-stranded nucleic acids binding to biomolecules configuring the biosample were affixed.

Further, after producing medicinally useful biomolecules of a biosample to construct a database, a serum profile of a specific person was generated and assayed with a program produced using an artificial neural network algorithm, thereby determining whether the person is afflicted or not with a cardiovascular disease or liver cancer and, if so afflicted, to determine what the cardiovascular disease is or whether or not the liver cancer has metastasized.

Useful spots were determined by comparison with databases constructed according to the disease type, and single-stranded nucleic acids corresponding to the spots were prepared, thereby separating and identifying proteins corresponding thereto.

EXAMPLE 10

Generation and Application of Profile of Surface Biomolecules of Cell Lines 10-1. Preparation of Biochip (Nucleic Acid Chip)

In the present invention, a biosample composed of two or more biomolecules was an example of cell lines.

A biochip for generating profiles of surface biomolecules of a non-small cell lung cancer cell line (biosample), according to the present invention, was prepared by the methods described in Examples 2 to 4. After reacting prepared random single-stranded nucleic acids with the lung cancer cell line, repetitively, cell line (biomolecule)-single-stranded nucleic acid complexes were washed with a washing buffer to dissociate unbound single-stranded nucleic acids and single-stranded nucleic acids depending on binding intensity thereof, and centrifuged at 5,000×g. Then, the cell line-single-stranded nucleic acid complexes were separated by centrifugation, thereby preparing single-stranded nucleic acids binding to the non-small cell lung cancer cell line.

Clones were selected from the prepared single-stranded nucleic acids, base sequenced, and analyzed, thereby selecting about 1,000 single-stranded nucleic acids. Capture probes having base sequences complementary to the selected about 1000 single-stranded nucleic acids were synthesized by the method of Example 2, and attached to a solid supporter, thereby preparing the nucleic acid chip according to the present invention.

10-2. Generation of Profile of Surface Biomolecules of Cell Line

A profile of surface biomolecules of a small cell lung cancer (SCLC) cell line was generated using the nucleic acid chip prepared by the method of Example 4. After reacting the small cell lung cancer cell line with a pool of single-stranded nucleic acids, biomolecule-single-stranded nucleic acid complexes of the cell line (biosample) were washed and separated. The single-stranded nucleic acids binding to the complexes were amplified and labeled by the method of Example 3. Capture probes and the labeled target probes were reacted with each other by the method of Example 4. A labeled substance bound to the target probes was measured by the method of Example 5, and a profile of surface biomolecules of the non-small cell lung cancer cell line was confirmed.

Figure 13:
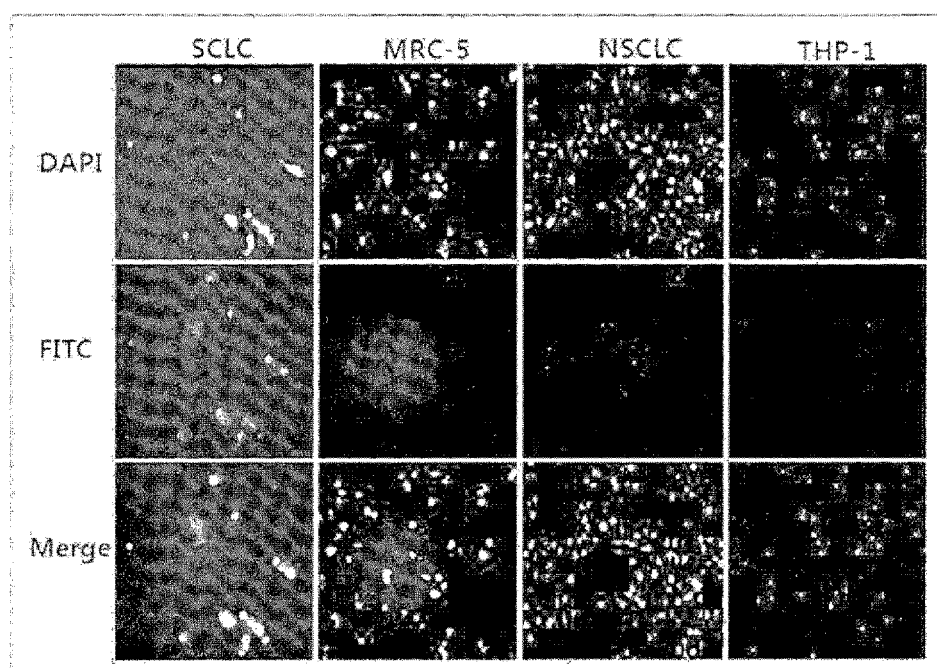
FIG. 13 is a view showing a result obtained by binding a single-stranded nucleic acid secured by generating and analyzing a surface biomolecule profile of a small cell lung cancer (SCLC) cell line generated using the nucleic acid according to the present invention and the small cell lung cancer cell line to each other.

Fluorescent images obtained by selecting single-stranded nucleic acids estimated to strongly bind to the small cell lung cancer (SCLC) cell line using the generated profile, synthesizing FITC-attached single-stranded nucleic acids, and reacting the synthesized FITC-attached single-stranded nucleic acids with the small cell lung cancer cell line, the non-small cell lung cancers (NSCLC) cell line, and blood cancer cell lines (MRC-5 and THP-1) are shown in FIG. 13.

As described above, it may be confirmed that the single-stranded nucleic acids selected by analyzing the profile of the small cell lung cancer cell line generated using the nucleic acid chip according to the present invention bound to the small cell lung cancer cell line.

EXAMPLE 11

Generation and Application of Profile of Surface Biomolecules of *E. coli*

11-1. Preparation of Biochip (Nucleic Acid Chip)

A nucleic acid chip according to the present invention was prepared using *E. coli* KCTC12006 (biosample) by the methods of Examples 2 to 4. After reacting prepared single-stranded nucleic acids with *E. coli*, repetitively, *E. coli* (biomolecule)-single-stranded nucleic acid complexes were washed with a washing buffer to dissociate unbound single-stranded nucleic acids and single-stranded nucleic acids depending on binding intensity thereof, and centrifuged at 5,000×g. Then, the *E. coli*-single-stranded nucleic acid complexes were separated by centrifugation, thereby preparing single-stranded nucleic acids binding to surface biomolecules of *E. coli*.

Clones were selected from the prepared single-stranded nucleic acids, base sequenced, and analyzed, thereby selecting about 1,000 single-stranded nucleic acids. Capture probes having base sequences complementary to the selected about 1000 single-stranded nucleic acids were synthesized and attached to a solid supporter, thereby preparing the nucleic acid chip according to the present invention.

11-2. Generation of Profile of Surface Biomolecules of *E. coli*

In the present invention, a biosample composed of two or more biomolecules was an example of bacteria.

A profile of surface biomolecules of *E. coli* KCTC12006 was generated using the nucleic acid chip prepared by the method of Example 6.

After reacting *E. coli* with a pool of single-stranded nucleic acids, *E. coli*-target single-stranded nucleic acid complexes were washed and separated. The single-stranded nucleic acids binding to the complexes were amplified and labeled by the method of Example 3. Capture probes and the labeled target probes were reacted with each other by the method of Example 4. The label substance bound to the target single-stranded nucleic acids was measured by the method of Example 5, and a profile of surface biomolecules of *E. coli* was confirmed.

Figure 14:
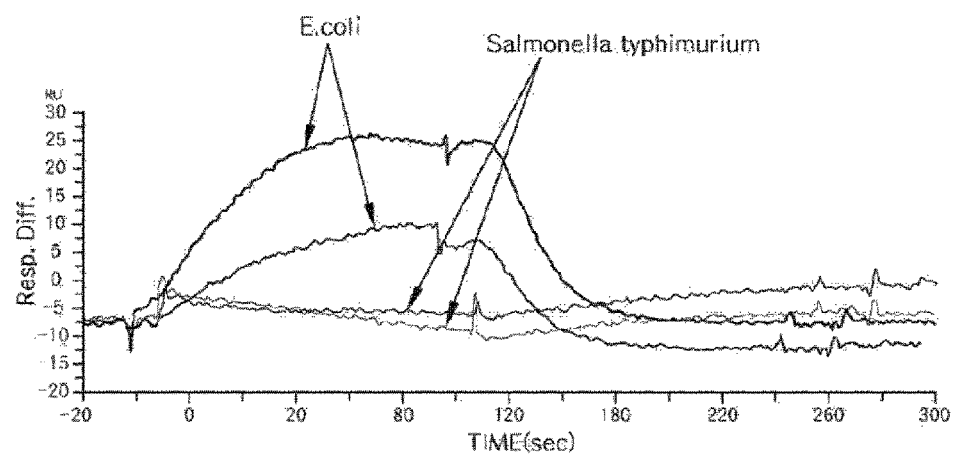
FIG. 14 is a view showing specificity of a biomolecule-binding single-stranded nucleic acid secured by generating and analyzing surface biomolecule profiles of *E. coli* KCTC12006 and *Salmonella typhimurium* ATCC13311 using the nucleic acid chip according to the present invention.

A profile of surface biomolecules of *Salmonella typhimurium* ATCC13311 was obtained by the same method as that used to generate the profile of the surface biomolecules of *E. coli*, thereby constructing a database therefor. Then, single-stranded nucleic acids specifically binding to *E. coli* were selected using a hierarchical clustering method. Specificity of the single-stranded nucleic acids was analyzed using an SPR device (BIAcore), and the results are shown in FIG. 14. It was confirmed that the selected single-stranded nucleic acids were specifically bound to *E. coli* as compared to *Salmonella typhimurium*.

Figure 15:
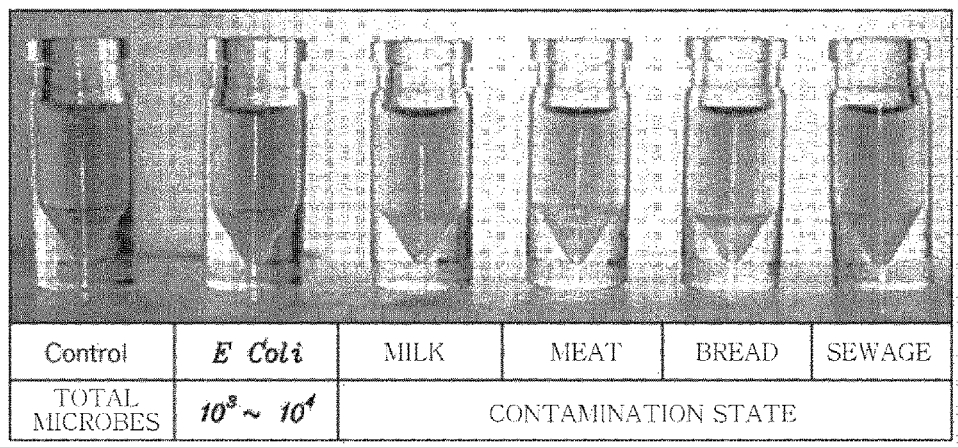
FIG. 15 is a view showing a result obtained by measuring degrees of contamination in foods contaminated with *E. coli*, using a biomolecule-binding single-stranded nucleic acid specifically binding to *E. coli*, selected using the nucleic acid chip according to the present invention, and nano gold particles.

The presence or absence of *E. coli* in a solution and a degree of contamination in food by *E. coli* were measured using the selected single-stranded nucleic acids by a method for measuring *E. coli* using single-stranded nucleic acids and gold nano-particles (e.g., see Korean Patent Application No. 10-2006-0072480), and the results are shown in FIG. 15. It was confirmed that in the case of reacting the single-stranded nucleic acids with a SELEX buffer with which the food had been washed, adding the gold nano-particles thereto, and adding a NaCl solution thereto, when there was no *E. coli*, a color of the solution was pale transparent blue, but when the solution was contaminated with *E. coli*, the color of the solution was changed to red. In addition, it was confirmed that the color intensity was proportional to the quantity of *E. coli*.

The exemplary embodiment of the present invention has been described above. Those skilled in the art will appreciate that the present invention may be implemented in a modified shape, without departing from the scope and spirit of the invention as disclosed in the accompanying claim. Therefore, the Examples described above should be considered in view of illustration rather than limitation. It should be interpreted that the scope of the present invention is defined by the following claims rather than the above-mentioned detailed description and all of differences within a scope equivalent thereto are included in the appended claims of the present invention.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for analyzing proteins in a biosample, the method comprising:
   (a) preparing the biosample for analysis;
   (b) quantifying two or more different proteins that are not present in the biosample as external reference substances and mixing the quantified proteins with the biosample with different quantified values;
   (c) treating the biosample mixed with the external reference substance with nucleic acid ligands specifically binding to target proteins in the biosample and the external reference substances, respectively, to induce formation of complexes between the target proteins in the biosample and the nucleic acid ligands and complexes between the external reference substance and the nucleic acid ligands;

(d) detecting nucleic acid ligands of the complexes for the target proteins and nucleic acid ligands of the complexes for the external reference substances, wherein step (d) includes:
(d-1) amplifying the nucleic acid ligands of the complexes for the target proteins and the nucleic acid ligands of the complexes for the external reference substance together with each other to prepare an analysis target probe; and
(d-2) detecting the analysis target probe, comprising the steps
(d-2-i) treating a biochip including a supporter and the following capture probes (i) and (ii) affixed onto the support with the analysis target probe to induce production of specific binding information between the capture probes and the analysis target probe,
(i) capture probes capturing target probes for the target proteins as single-stranded nucleic acids; and
(ii) a capture probe capturing a target probe for the external reference substance as a single-stranded nucleic acid, and
(d-2-ii) determining the presence or absence and quantities of the target proteins in the biosample from the specific binding information,
wherein step (d-2-i) is performed by amplifying nucleic acid ligands having the same sequences as those of the nucleic acid ligands of the complexes for the target proteins, amplifying nucleic acid ligands having the same sequences as those of the nucleic acid ligands of the complexes for the external reference substance, and quantifying and mixing two kinds of amplification products to prepare a comparison target probe, quantifying the comparison target probe and mixing the quantified comparison target probe with the analysis target probe, and treating the biochip with a mixed target probe containing the comparison target probe and the analysis probe,
the comparison target probe being labeled with Cy3 or Cy5, and
the analysis target probe being labeled with Cy5 or Cy3, different from the comparison target probe; and
(e) comparing detection results of nucleic acid ligands with respect to the target proteins and detection results of nucleic acid ligands with respect to the external reference substances, obtained in step (c), and quantifying the target proteins in the biosample,
wherein the different quantified values of the two or more of external reference substances are used to quantitatively analyze the target proteins.

2. The method of claim 1, wherein all of the nucleic acid ligands include a region specifically binding to the target protein or the external reference substance, an already known sequence region binding to a forward primer at an upstream thereof, and an already known sequence region binding to a reverse primer at a downstream thereof, and
the sequence region binding to the forward primer and the sequence region binding to the reverse primer exist as the same sequences in all of the nucleic acid ligands, such that amplification in step (d-1) is performed using a pair of primers.

3. The method of claim 2, wherein the region specifically binding to the target protein or the external reference substance has a length enough to enable specific binding to the target protein or the external reference substance.

4. The method of claim 1, wherein the nucleic acid ligand is a single-stranded nucleic acid.

5. The method of claim 1, wherein the nucleic acid ligand is a single-stranded RNA.

6. The method of claim 1, wherein the target protein is an unknown target protein, an already known target protein, or a mixture thereof.

* * * * *

SEQUENCE LISTING

```
<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Bind region of a primer

<400> SEQUENCE: 1
gggagagcgg aagcgtgctg ggcc                                              24

<210> SEQ ID NO 2
<211> LENGTH: 28
<212> TYPE: DNA
<213> ORGANISM: Artificial Sequence
<220> FEATURE:
<223> OTHER INFORMATION: Bind region of a primer

<400> SEQUENCE: 2
cataacccag aggtcgatgg atcccccc                                          28

<210> SEQ ID NO 3
<211> LENGTH: 17
<212> TYPE: DNA
<213> ORGANISM: Artificial Sequence
<220> FEATURE:
<223> OTHER INFORMATION: primer

<400> SEQUENCE: 3
cggaagcgtg ctgggcc                                                      17

<210> SEQ ID NO 4
<211> LENGTH: 17
<212> TYPE: DNA
<213> ORGANISM: Artificial Sequence
<220> FEATURE:
<223> OTHER INFORMATION: primer

<400> SEQUENCE: 4
cggaagcgtg ctgggcc                                                      17

<210> SEQ ID NO 5
<211> LENGTH: 92
<212> TYPE: DNA
<213> ORGANISM: Artificial Sequence
<220> FEATURE:
<223> OTHER INFORMATION: Oligonucleotide with random base sequence
<220> FEATURE:
<221> NAME/KEY: misc_feature
<222> LOCATION: (25)..(64)
<223> OTHER INFORMATION: n is a, c, g, or t

<400> SEQUENCE: 5
gggagagcgg aagcgtgctg ggccnnnnnn nnnnnnnnnn nnnnnnnnnn nnnnnnnnnn        60
nnnncataac ccagaggtcg atggatcccc cc                                     92
```